United States Patent
Inan et al.

(10) Patent No.: US 11,039,782 B2
(45) Date of Patent: Jun. 22, 2021

(54) WEARABLE TECHNOLOGIES FOR JOINT HEALTH ASSESSMENT

(71) Applicant: Georgia Tech Research Corporation, Atlanta, GA (US)

(72) Inventors: Omer T. Inan, Atlanta, GA (US); Michael N. Sawka, Atlanta, GA (US); Jennifer O. Hasler, Atlanta, GA (US); Hakan Toreyin, Atlanta, GA (US); Mindy L. Millard-Stafford, Atlanta, GA (US); Geza Kogler, Atlanta, GA (US); Sinan Hersek, Atlanta, GA (US); Caitlin Teague, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 151 days.

(21) Appl. No.: 15/577,253

(22) PCT Filed: May 27, 2016

(86) PCT No.: PCT/US2016/034874
§ 371 (c)(1),
(2) Date: Nov. 27, 2017

(87) PCT Pub. No.: WO2016/191753
PCT Pub. Date: Dec. 1, 2016

(65) Prior Publication Data
US 2018/0160966 A1    Jun. 14, 2018

Related U.S. Application Data

(60) Provisional application No. 62/166,889, filed on May 27, 2015.

(51) Int. Cl.
*A61B 5/053* (2021.01)
*A61B 5/00* (2006.01)
(Continued)

(52) U.S. Cl.
CPC ............ *A61B 5/4585* (2013.01); *A61B 5/026* (2013.01); *A61B 5/0295* (2013.01); *A61B 5/053* (2013.01);
(Continued)

(58) Field of Classification Search
None
See application file for complete search history.

(56) References Cited

U.S. PATENT DOCUMENTS

2004/0158167 A1    8/2004    Smith et al.
2007/0179739 A1    8/2007    Donofrio et al.
(Continued)

FOREIGN PATENT DOCUMENTS

JP    2009-542294    12/2009
JP    2012183294 A    9/2012
(Continued)

OTHER PUBLICATIONS

Extended Search Report from European Application No. 16800844.9 dated Dec. 10, 2018 (9 pages).
(Continued)

*Primary Examiner* — Eric F Winakur
*Assistant Examiner* — Marjan Fardanesh
(74) *Attorney, Agent, or Firm* — Troutman Pepper Hamilton Sanders LLP; Ryan A Schneider

(57) ABSTRACT

Multi-modal sensing relating to joint acoustic emission and joint bioimpedance. Custom-design analog electronics and electrodes provide high resolution sensing of bioimpedance, microphones and their front-end electronics for capturing sound signals from the joints, rate sensors for identifying joint motions (linear and rotational), and a processor unit for interpretation of the signals. These components are packed into a wearable form factor, which also encapsulates the
(Continued)

hardware required to minimize the negative effects of motion artifacts on the signals.

28 Claims, 13 Drawing Sheets

(51) Int. Cl.
  *A61B 7/00* (2006.01)
  *A61B 5/0537* (2021.01)
  *A61B 5/0295* (2006.01)
  *A61B 5/026* (2006.01)
  *A61B 5/11* (2006.01)

(52) U.S. Cl.
  CPC .......... *A61B 5/0537* (2013.01); *A61B 5/1116* (2013.01); *A61B 5/1123* (2013.01); *A61B 5/4528* (2013.01); *A61B 5/4878* (2013.01); *A61B 5/6828* (2013.01); *A61B 7/006* (2013.01); *A61B 2562/0204* (2013.01)

(56) References Cited

U.S. PATENT DOCUMENTS

| | | | |
|---|---|---|---|
| 2009/0024065 | A1 | 1/2009 | Einarsson |
| 2012/0029345 | A1 | 2/2012 | Mahfouz et al. |
| 2012/0190989 | A1 | 7/2012 | Kaiser et al. |
| 2014/0128939 | A1 | 5/2014 | Embrey et al. |
| 2016/0015972 | A1* | 1/2016 | Hyde .................. A61B 5/4585 607/48 |

FOREIGN PATENT DOCUMENTS

| | | |
|---|---|---|
| JP | 2013-502278 | 1/2013 |
| WO | 2008004159 | 1/2008 |
| WO | 2010007383 A2 | 1/2010 |
| WO | 2011022418 | 2/2011 |
| WO | 2011-096419 | 8/2011 |
| WO | 2015/002935 | 1/2015 |
| WO | 2015/088863 | 6/2015 |
| WO | 2015/063520 | 7/2015 |

OTHER PUBLICATIONS

International Preliminary Report on Patentabiliby from application No. PCT/US2016/034874, dated Dec. 7, 2017 (10 pages).
Search Report and Written Opinion from PCT Application No. PCT/US16/034874 dated Sep. 14, 2016 (14 pages).
Office Action from Application No. JP 2017-561251 dated Jun. 17, 2020 ( 8 pages, including 4 pages of English translation).
Decision of Refusal in Application No. JP 2017-561251 dated Feb. 8, 2021 ( 6 pages, including 3 pages of English translation).

* cited by examiner

WEARABLE TECHNOLOGIES FOR JOINT HEALTH ASSESSMENT

CROSS-REFERENCE TO RELATED APPLICATIONS

This application is a U.S. National Stage of International Patent Application No. PCT/US2016/034874, filed May 27, 2015, entitled "Wearable Technologies for joint Health Assessment", which claims priority to U.S. Provisional Patent Application No. 62/166,889, filed May 27, 2015, the contents of of which are all fully incorporated herein by reference.

STATEMENT REGARDING FEDEALLY SPONSORED RESEARCH

This invention was made with government support under Grant No. W911NF14C0058, aweareded by The U.S. Army. The government has certain rights in the invention

BACKGROUND OF THE INVENTION

1. Field of the Invention

The present invention relates to health systems and methods, and more particularly to a wearable system and method that assesses the health status of a user's joint and informs the user and/or caregiver of the results.

2. Description of Related Art

The knee is subject to major stresses during normal daily life as well as athletic activities with multidirectional forces exerted on the joint during movement. As a result, the knee represents not only one of the most frequently injured body parts but also accounts for many severe injuries in terms of time of restricted and/or total loss of participation among athletes, military personnel, and other populations engaged in high performance activities.

Knee injuries are not exclusive to active populations; sedentary populations may be at higher risk for such injuries due to poor cardiovascular health, atrophied surrounding muscles which fail to properly stabilize the joint, and lack of training and warm-up.

This frequency across populations combined with the extensive treatment requirements-often entailing surgery and/or substantial rehabilitation-result in approximately 10.4 million patient visits annually in the United States. To this extent, these injuries are considerable in their effect on not only the health care system but also on patients' daily lives given the knee's significance in performing ambulatory motions and other everyday activities.

Joint disorders are highly prevalent and limit physical activity, which may cause reduced quality of life. Symptoms that are common to many joint disorders are swelling, increased blood flow, and reduced movement capability. In clinical conditions, the joint health is assessed based on qualitative observations of the clinician; standard examinations do not yield any quantitative feedback to the physician or patient regarding, for example, the swelling, range of motion, or structural integrity of the joint. Examination methods based on diagnostic imaging do provide quantitative metrics of joint health, but are less commonly used because they are expensive and time consuming.

Beyond the clinic, such as in the home or with wearable technologies, there are no viable solutions available for providing in-depth, quantitative joint health assessment. Wearable assistive technologies for monitoring joint health can help rehabilitating injured patients perform physical therapy and assess their progress in the comfort of their home, or collect objective clinical data during unsupervised rehabilitation programs in athletes and soldiers, provided that the devices are unobtrusive and accurate.

Thus, to alleviate such strains on the health care system and facilitate monitoring of patients during daily activities, researchers have explored the use of wearable devices to unobtrusively acquire health information. With regard to musculoskeletal and biomechanical-related disorders and injuries, these systems provide new ways to collect objective and quantitative data.

Acoustics can provide an unobtrusive method-and thus a possible wearable platform-for capturing information regarding underlying physical structures and alignments, articulating surfaces, and soft tissue characteristics. Friction between the structures and articulating components of the knee joint gives rise to various kinds of vibrations. These vibrations (i.e., acoustical energy) travel to the skin surface where they encounter a large impedance mismatch between the fluid-filled tissue and air. Because of this, most of the acoustical energy manifests itself as vibrations signals on the skin with the majority of the energy reflected back into the tissue.

However, there is a small amount of energy that propagates to the air, resulting in audible joint sounds. While some early work in this area studied airborne signals using "air" microphones, the majority of research has largely utilized vibration sensors as "contact" microphones (e.g., accelerometers, piezoelectric devices, stethoscopes) to measure joint sound vibrations.

Researchers have concentrated on the efficacy of joint acoustic emissions, or vibroarthographic signals (VAG), as clinically-relevant biomarkers for joint health, and notably, the majority of the research has worked towards developing diagnostic techniques to differentiate "healthy" vs. "unhealthy" knee joints, primarily as it concerns cartilage-based conditions such as osteoarthritis and chondromalacia.

Research has included measuring acoustic emissions from the knee using a condenser microphone and captured low frequency signals (<100 Hz), and using wide-band piezoelectric sensors to record emissions in the ultrasonic band (>20 kHz). This research observed differences between healthy knees and those afflicted with osteoarthritis and found that osteoarthritic knees produce more frequent, higher peak, and longer duration acoustic emissions compared to healthy knees. Osteoarthritic subjects were also evaluated using an accelerometer and led to the classification of three different conditions of the patellofemoral joint. To achieve such outcomes, significant work has been devoted to developing various signal processing techniques for conditioning and classifying VAG signals. Algorithms have leveraged linear prediction and autoregressive modeling, statistical parameter investigation, Fourier and time-frequency analysis, wavelet decomposition, and neural networks and other classifier methods such as dynamic weighted classifier fusion.

Another recent technology that has been investigated for local joint health assessment is electrical bioimpedance (EBI). EBI has been demonstrated as a possible means of evaluating knee osteoarthritis, edema (swelling) related to lower limb muscle injuries, and edema for total knee arthroplasty surgery and rehabilitation.

For EBI measurements, a small electrical current is injected into a volume of tissue-such as the volume of tissue encapsulating a knee joint-and the resultant voltage drop across the tissue is measured. The ratio of this voltage to the injected current yields the electrical impedance of this tissue, and can change based on the structural composition of the medium (e.g. increased edema decreases the tissue impedance since fluid is less resistive than muscle, fat, or bone).

EBI has also been used in cardiovascular physiology research as a means of quantifying blood flow and volume, such as for estimating cardiac output or the local blood flow rate to (or blood volume pulse at) a limb. While EBI measurements for structural assessment typically examine the static (varying over the course of hours to days) component of tissue impedance, measurements for cardiovascular assessment examine the dynamic (varying over the course of milliseconds) components.

Additionally, while static EBI measurements involve magnitudes of changes on the order of 1 s to 10 s of Ohms, dynamic cardiovascular measures from limbs can be as small as 10 s of milli-Ohms. Accordingly, the performance of the analog front-end circuitry for EBI measurements becomes significantly more challenging when targeting both static and dynamic measurements.

Nevertheless advances over the past several years have been made in EBI circuit and system design, including improving the current source for high frequency implementation, increasing the output impedance and accuracy of complementary metal-oxide semiconductor (CMOS) current drivers for EBI, developing error correction algorithms, and investigating solutions for textile electrode interfaces. In the literature, such dynamic measurements of limb impedance are referred to as impedance plethysmography (IPG).

In addition to quantifying edema with static EBI, quantifying the local blood flow patterns following a joint injury with IPG could provide significant insight into joint rehabilitation progress. An increase in local blood flow may follow an injury to the joint, associated with inflammation and scar tissue formation, while decrease in local blood flow may be indicative of improving status. Such changes in blood flow patterns are believed to precede changes in structure (edema) or range of motion, and can potentially provide early biomarkers for changing joint health status.

Beyond local blood flow, IPG measurements can also provide a window to evaluating the overall cardiovascular physiology and autonomic nervous system (ANS) balance through heart rate variability (HRV), thus providing an index of a person's sympathetic arousal which has been shown to increase in response to pain.

However, no existing bioimpedance technologies are capable of providing both the required resolution to capture edema measures and blood flow, and operate on sufficiently low power consumption such that several hours of use on a small battery is feasible.

It would be beneficial to find solutions to the above deficiencies in conventional monitoring and assessment technologies, providing systems and methods that can provide around-the-clock monitoring of joint acoustics and bioimpedance during normal activities of daily living, and prescribed rehabilitation activities that elicit specific signatures indicative of improving or worsening joint health.

It is to the provision of such systems and methods using miniature sensors that can be readily integrated into a wearable device enabling, for the first time, wearable joint acoustics and bioimpedance sensing that are primary objects of the present invention.

BRIEF SUMMARY OF THE INVENTION

In an exemplary embodiment of the present invention, the present invention quantifies the degree of injury at a joint through observation of joint disorder symptoms by accurately monitoring two sensing modalities, and interpreting them in the context of joint motion. For example, the multi-modal sensing can include at-home monitoring sensing regimes for one type of joint characteristic, like joint acoustic emission, wherein the multi-modal sensing incorporates contact-based and non-contact based (airborne) measurement of joint acoustic emission system. Other types of joint characteristics include joint edema and blood flow assessments. These joint characteristics can be investigated via vector bioimpedance measurements.

In another example, the multi-modal sensing can include at-home monitoring sensing regimes for more than one type of joint characteristic, for instance both joint acoustic emission and joint bioimpedance measurements.

In an exemplary embodiment of the present invention, wherein the multi-modal sensing relates to one type of joint characteristic, like joint acoustic emission, the invention can comprise systems and methods of wearable joint rehabilitation assessment following musculoskeletal injury using three types of sensors to obtain joint sounds in healthy collegiate athletes during unloaded flexion/extension. The sensors can comprise microphones, and include more than one type of microphone. In exemplary embodiments, one or more microphone types are selected from the group consisting of electret, MicroElectrical-Mechanical System (MEMS), and piezoelectric film microphones.

Joint sounds in healthy collegiate athletes during unloaded flexion/extension were investigated, and the robustness of each microphone's measurements evaluated via: (i) signal quality and (ii) within-day consistency. It was found that air microphones acquired higher quality signals than contact microphones (signal-to-noise-and-interference ratio of 11.7 dB and 12.4 dB for electret and MEMS, respectively, vs. 8.4 dB for piezoelectric). Furthermore, air microphones measured similar acoustic signatures on the skin and 5 cm off the skin (~4.5× smaller amplitude). It was also found that the main acoustic event during repetitive motions occurred at consistent joint angles (the intraclass correlation coefficient (ICC) (1, 1)=0.94 and ICC(1, k)=0.99). Additionally, it was found that this angular location was similar between right and left legs, with asymmetry observed in only a few individuals.

In one embodiment, air microphones are used for wearable joint sound sensing, where for practical implementation of contact microphones in a wearable device, interface noise must be reduced. Airborne signals can be measured consistently and healthy left and right knees often produce a similar pattern in acoustic emissions.

In an exemplary embodiment of the present invention, wherein bioimpedance measurements are examined, a robust vector bioimpedance measurement system leveraging embedded systems concepts for longitudinal knee joint health assessment are used. The systems and methods can comprise a custom analog front-end based on discrete components to achieve high resolution static (slowly varying over the course of hours to days) and dynamic (rapidly varying on the order of milli-seconds) bioresistance and bioreactance measurements within a footprint and power consumption feasible for a wearable, on-body implementation.

In one embodiment, occupying an area of 64×48 mm$^2$ and consuming 0.66 W when supplied with ±5 V, the front-end achieves a dynamic range of 345Ω and noise floor of 0.018 mΩ$_{rms}$ (resistive) and 0.055 mΩ$_{rms}$ (reactive) within a bandwidth of 0.1-20 Hz. A microcontroller allows real-time calibration to minimize errors in measurements due to environmental variability (e.g. temperature) that can be experienced outside of clinical or lab environments, and enables data storage on a micro secure digital (SD) card. The acquired signals are then processed using customized physiology-driven algorithms to extract musculoskeletal (edema) and cardiovascular (local blood volume pulse) features from the knee joint.

Statistically significant differences (p<0.01) were found between the injured and contralateral static knee impedance measures for two subjects with recent unilateral knee injury compared to seven controls. Specifically, the impedance was lower for the injured knees, supporting the physiological expectations for increased edema and damaged cell membranes. Further, the sensitivity of the dynamic impedance measures with a cold pressor test were demonstrated, with a 20 mΩ decrease in the pulsatile resistance and 0.2 Ω/s decrease for the time derivative of resistance associated with increased downstream peripheral vascular resistance.

In another exemplary embodiment of the present invention, the multi-modal sensing relates to more than one type of joint characteristic, for example both joint acoustic emission and joint bioimpedance, the more than one sensing modalities are interpreted in the context of joint motion. The present invention can comprise custom-design analog electronics and electrodes for high resolution sensing of bioimpedance, microphones and their front-end electronics for capturing sound signals from the joints, rate sensors for identifying joint motions (linear and rotational), and a processor unit for interpretation of the signals. These components are packed into a wearable form factor, which also encapsulates the hardware required to minimize the negative effects of motion artifacts on the signals.

The present invention makes use of bioimpedance measurements to monitor the amount of swelling and the blood flow rate at the joint. To measure changes in slow-varying fluid volume and fast-varying blood flow rate, the bioimpedance hardware outputs both static and dynamic components of the joint bioimpedance, which has a resistive and reactive component. To detect even small changes in blood flow rate, the bioimpedance hardware is a custom-designed analog front-end with improved noise performance.

The bioimpedance measurements are done by delivering current to the joint site through the electrodes, which are in quadripolar configuration to reduce the effect of electrode-skin interface impedance, and measuring the potential difference across the joint through amplification and phase-sensitive detection stages. The static and dynamic components are later separated by a filter stage at the output. The injected current magnitude is below a safety threshold that does not create damage at the measurement site, and its frequency is such that it can propagate through both intra and extra-cellular fluids.

Under motion, joints emit acoustical waves propagating through the tissue. Depending on the fluid content of the joint, various parameters (e.g., rms power, frequency content) of the waveforms change. The present invention incorporates measurements to record the acoustical emissions and extract joint-health-related features from the changes in sound waveform parameters. Contact microphones are used to capture the sound waves originated by the mechanical vibrations. To improve the noise performance and therefore accuracy of the system, airborne microphones that are more immune to noise originated from the skin-microphone interface, are used in a complementary manner. In general, the microphones are placed around the joint but the exact number and positions vary with the joint of interest. Custom-designed analog front-end circuitry is used to amplify and filter the sound signals to further improve the noise performance.

Joints are dynamic structures by their nature, and therefore the system performs activity-contextualized joint health assessment. To autonomously classify the joint motion with its parameters (i.e., range-of-motion, frequency), the present invention makes use of rate sensors that are placed on the moving parts of the joint of interest. The activity classification is also used to improve the energy-efficiency of the system while operating with minimum user intervention-the system wakes up from a sleep-mode only when the user performs certain activities to be pre-defined by the clinician.

Designed to be worn on the body and used under unsupervised conditions, the system hosts smart packaging elements (e.g., thin contact pressure sensors at the skin-sensor interfaces) that minimize the effects of motion artifacts on the measured signals.

A central processor unit processes all sensory data to extract joint-health-related features. The processing is done in digital, analog, or mixed-signal domains using multipurpose devices (e.g., microprocessor, field-programmable analog array) or custom-designs (e.g., application-specific integrated circuit, discrete circuit). The present invention informs the user and/or caregiver of the status of the joint health that the processor outputs.

In another exemplary embodiment, the present invention comprises systems and methods to decide if a user of an exemplary wearable system of the present invention is in an acceptable position for bioimpedance measurements to be taken or not. Since bioimpedance measurements are greatly impacted by motion artifacts, subject position, electromagnetic interference and voltage fluctuations of the skin electrode interference, an innovative solution is needed to provide consistency that measurements should be taken when subject is still in a given position and in the absence of electromagnetic interference and skin electrode interface related fluctuations (such as an electrode loosing contact with the skin). The present invention can provide a solution by presenting inertial measurement units along with the dynamic resistance (impedance plethysmography) signals that are used together to decide if the user is in an acceptable position for bioimpedance measurements to be taken or not.

In another exemplary embodiment, the present invention is a system for assessing joint health comprising a first sensing assembly for sensing characteristics related to joint physiology, a second sensing assembly for sensing characteristics related to joint structure, and a health assessor that provides an assessment of joint health through interpretation of characteristics from the first and the second sensing assemblies.

The system can further comprise an output assembly capable of providing an indication of joint health to a user of the system.

The first sensing assembly can comprise wearable acoustic sensors to measure acoustic emissions from the joint during movement. The first sensing assembly comprises wearable sensors to measure at least one non-acoustic characteristic of joint movement. A non-acoustic characteristic of joint movement can be selected from the group consisting of linear acceleration and angular velocity.

The first sensing assembly can comprise wearable sensors to measure linear acceleration and angular velocity of joint movement.

The second sensing assembly can comprise wearable sensors to measure bioimpedance of the joint. The wearable sensors to measure bioimpedance of the joint can comprise at least four surface electrodes configured to measure proximal EBI of tissue and blood in proximity of the joint.

In another exemplary embodiment, the present invention is a system for assessing joint health comprising a first sensing assembly for sensing characteristics related to joint physiology, the first sensing assembly comprising acoustic sensors to measure acoustic emissions from the joint during movement, and sensors to measure at least one non-acoustic characteristic of joint movement selected from the group consisting of linear acceleration and angular velocity, a second sensing assembly for sensing characteristics related to joint structure comprising sensors to measure bioimpedance of the joint, a health assessor that provides an assessment of joint health through interpretation of characteristics from the first and the second sensing assemblies, and an output assembly capable of providing an indication of joint health to a user of the system.

At least a portion of the acoustic sensors can comprise wearable acoustic sensors for placement proximate the joint. At least a portion of the acoustic sensors can comprise sensors for placement distal the joint.

The sensors to measure at least one non-acoustic characteristic of joint movement and the sensors to measure bioimpedance of the joint can comprise wearable sensors for placement proximate the joint.

The wearable sensors to measure bioimpedance of the joint can comprise at least four surface electrodes configured to measure EBI of tissue and blood proximate the joint.

The wearable acoustic sensors can comprise piezoelectric film and are capable of measuring surface vibrations of the skin associated with acoustic emissions from the joint.

The acoustic sensors distal the joint can comprise microphones capable of measuring airborne acoustic emissions from the joint.

At least a portion of the acoustic sensors can comprise wearable acoustic sensors for placement proximate the joint capable of measuring surface vibrations of the skin associated with acoustic emissions from the joint, wherein the sensors to measure at least one non-acoustic characteristic of joint movement and the sensors to measure bioimpedance of the joint can comprise wearable sensors for placement proximate the joint, and wherein at least a portion of the acoustic sensors can comprise microphones distal the joint and capable of measuring airborne acoustic emissions from the joint.

At least a portion of the wearable sensors can comprise surface silver/silver-chloride (Ag/AgCl) gel electrodes.

At least a portion of the wearable sensors can comprise capacitive dry electrodes.

At least a portion of the wearable sensors can comprise textile electrodes.

In another exemplary embodiment, the present invention is a system for assessing joint health comprising a first sensing assembly for sensing characteristics related to joint physiology, the first sensing assembly comprising acoustic sensors capable of sending at least one signal representative of acoustic emissions from the joint during movement, and sensors capable of sending at least one signal representative of at least one non-acoustic characteristic of joint movement selected from the group consisting of linear acceleration and angular velocity, a second sensing assembly for sensing characteristics related to joint structure comprising sensors capable of sending at least one signal representative of bioimpedance of the joint, a health assessor comprising at least one processor that provides an assessment of joint health through processing the signals from the first and the second sensing assemblies, and an output assembly capable of providing an indication of the joint health from the health assessor to a user of the system.

The second sensing assembly can further comprise an electronic interface to the sensors capable of sending at least one signal representative of bioimpedance of the joint.

At least one of the health assessor processors can automatically and periodically calibrates the bioimpedance measurements using electronic loads and an algorithm.

At least one of the health assessor processors can process at least one signal representative of acoustic emissions from the joint in the context of joint angle.

At least one of the health assessor processors can process acoustic emissions from the joint using filter banks to separate signals based on frequency content.

At least one of the health assessor processors can detect a type of activity occurring in proximity to the joint, and processes acoustic emissions from the joint during the activity based on the type of activity. A type of activity can be selected from the group consisting of unloaded knee flexion/extension exercise, sit-to-stand exercise, walking, and stair-climbing.

At least one of the health assessor processors can process at least one signal representative of bioimpedance of the joint, which processing provides an indication of joint swelling.

At least one of the health assessor processors can process at least one signal representative of bioimpedance of the joint, which processing provides an indication of blood flow proximate the joint.

At least one of the health assessor processors can process at least one signal representative of bioimpedance of the joint, which processing provides an indication of blood volume proximate the joint.

In another exemplary embodiment, the present invention is a wearable system for assessing joint health of a user comprising a first sensing modality assembly for sensing characteristics related to joint physiology, a second sensing modality assembly for sensing characteristics related to joint structure, and a health assessor that quantifies a degree of injury at the joint through interpretation of characteristics from the first and the second sensing modality assemblies.

The system can further comprise an output assembly capable of providing an indication of joint health to the user of the system. The system can further comprise an output assembly capable of providing an indication of joint health to a care giver of the user of the system.

The first sensing modality assembly can comprise an acoustical assembly.

The second sensing modality assembly can comprise a bioimpedance assembly.

The acoustical assembly and health assessor can be capable of determining acoustical emissions proximate the joint and distal the joint.

The bioimpedance assembly and health assessor can be capable of determining joint swelling.

The bioimpedance assembly and health assessor can be capable of determining blood flow proximate the joint.

The bioimpedance assembly and health assessor can be capable of determining blood volume proximate the joint.

In another exemplary embodiment, the present invention is a system for assessing joint health of a user comprising a first sensing modality assembly for sensing characteristics related to joint physiology, the first sensing modality assembly comprising an acoustical assembly including wearable proximate joint acoustic sensors capable of sending at least one signal representative of acoustic emissions from the joint during movement, distal joint acoustic sensors capable of sending at least one signal representative of airborne acoustic emissions from the joint during movement, and wearable proximate joint sensors capable of sending at least one signal representative of at least one non-acoustic characteristic of joint movement selected from the group consisting of linear acceleration and angular velocity, a second sensing modality assembly for sensing characteristics related to joint structure, the second sensing modality assembly comprises a bioimpedance assembly, and a health assessor that provides an assessment of joint health through processing of characteristics from the first and the second sensing assemblies.

The bioimpedance assembly and health assessor can be capable of determining characteristics related to joint structure selected from the group consisting of joint swelling, blood flow, and blood volume.

The bioimpedance assembly can comprises a source of current and a receiver, and a processor capable of measuring the potential difference across the joint through amplification and phase-sensitive detection stages.

The source of current comprises electrodes.

The source of current can be capable of delivering current to the joint through the electrodes.

The source of current can deliver current below a safety threshold that does not create damage at the joint.

The source of current can deliver current at a frequency such that it can propagate through both intra and extra-cellular fluids.

The electrodes can comprise a quadripolar configuration to reduce the effect of electrode-skin interface impedance.

The blood flow characteristic can comprise a static component and a dynamic component.

The static component of the blood flow characteristic can relate to relatively slow-varying fluid volume.

The dynamic component of the blood flow characteristic can relate to relatively fast-varying blood flow rate.

The wearable proximate joint acoustic sensors can comprise contact microphones that capture sound waves originated by mechanical vibrations in proximity of the joint.

These and other objects, features and advantages of the present invention will become more apparent upon reading the following specification in conjunction with the accompanying drawing figures.

DETAIL DESCRIPTION OF THE INVENTION

Figure 1:
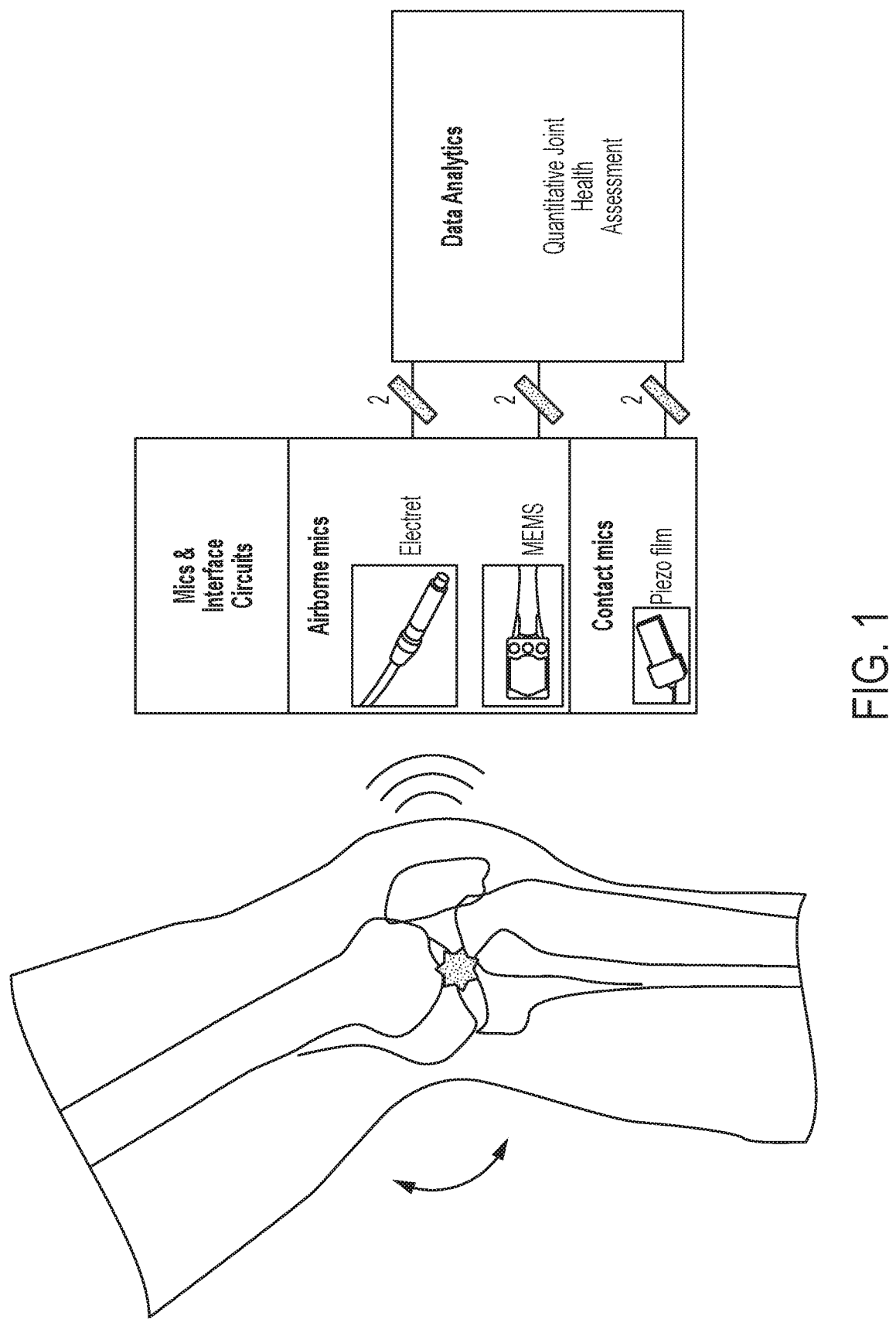
FIG. 1 is a block diagram of knee joint acoustic emissions sensing and interpretation for quantifying joint health during rehabilitation according to an exemplary embodiment of the present invention.

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described as making up the various elements of the invention are intended to be illustrative and not restrictive. Many suitable materials that would perform the same or a similar function as the materials described herein are intended to be embraced within the scope of the invention. Such other materials not described herein can include, but are not limited to, for example, materials that are developed after the time of the development of the invention.

Methods for Sensing Acoustical Emissions from the Knee for Wearable Joint Health Assessment In an exemplary embodiment of the present invention, wherein the multi-modal sensing relates to one type of joint characteristic, like joint acoustic emission, the invention can comprise systems and methods of wearable joint rehabilitation assessment following musculoskeletal injury using miniature sensors readily integrated into a wearable device enabling, for the first time, wearable joint acoustics sensing (FIG. 1).

Microphone Selection

When investigating types of sensors to use in the present invention, the following were considered: (i) their ability to sense acoustic emissions, and (ii) their practicality for integration within a wearable system. Analysis of how joint sounds propagate through the tissue and transmit to the air suggest contact microphones are the most appropriate sensor for acquiring joint sounds, and a review of conventional systems illustrated that most research employed contact microphones successfully in clinical/lab applications. A contact microphone should theoretically acquire the highest quality acoustic signal since it senses the original, non-attenuated signal and is not sensitive to background noise.

However, during motion and unsupervised at-home activity, loss of the sensor-to-skin interface is likely and of significant concern, for any compromise to the interface will be detrimental to the signal. In the extreme case that the sensor loses contact with the skin, the system will be unable to record joint sounds completely.

To improve robustness, air microphones provide complementary sensing capabilities. The signal obtained by air microphones is inherently different from contact microphones. Air microphones will only detect the airborne sounds: attenuated, higher frequency signals. Additionally, while not limited by the sensor-to-skin interface like contact microphones, air microphones are much more susceptible to background noise. For these reasons, the present invention employed both sensing modalities-contact and air microphones-to more robustly capture the acoustic emissions from the joint in a wearable device.

For the contact microphone, a piezoelectric film (SDT, Measurement Specialties, Hampton, Va., US) was selected because its form factor seemingly lends itself to a wrap and other devices conventionally worn on the knee. Furthermore, piezoelectric films have wider bandwidths compared to miniature, low cost accelerometers, allowing for sensing of high frequency audio signals.

Two types of air microphones were selected to supplement the piezoelectric film in acquiring acoustic emissions from the knee joint. The first was a commercially-available electret microphone (Sanken Microphone Co., Ltd., Japan). The second was a MEMS microphone, specifically the MP33AB01 (STMicroelectronics, Geneva, Switzerland), which was mounted on a custom PCB.

Electret and MEMS microphones sense sounds in a similar manner; however, the commercial electret microphone is much more expensive (~100×) compared to the MEMS microphone. The MEMS's low-cost and sensing capabilities provide a more realistic solution for implementation in a wearable device; however, both the electret and MEMS microphones were used during experiments with the electret microphone acting as the industry standard in terms of the quality of the sound acquired. Recordings from the air microphones were of primary focus because presently they provide higher quality recordings.

Methods for Microphone Comparison

The similarity of the MEMS and electret microphones in detecting knee joint acoustic emissions was quantified by computing the information radius between the normalized histograms of these signals, which were acquired by both sensors at the same time placed in the same location on the lateral side of the patella. To construct the aforementioned histograms, the signals acquired from the microphones were first normalized such that their amplitudes were limited to the range [0, 1]. The histogram was formed from this normalized signal using 1000 bins.

Next, the quality of each sensor was evaluated by computing the signal-to-noise-and-interference ratio (SNIR). The SNIR for each microphone was calculated by finding the ratio of the peak power of a "click" (i.e., acoustic emission) emitted by the knee joint to the peak power of interface noise in the vicinity of the click. For this calculation, acoustic emissions from the microphones positioned at the medial side of the patella for the air microphones and distal side of the patella for the contact microphone were used.

Lastly, a proof-of-concept experiment was conducted to compare signals measured on and off of the skin. A subject performed three cycles of seated, unloaded knee flexion/extension with two electret microphones positioned at the lateral side of the patella, one on the skin and one located 5 cm off the skin. The resulting signals were then compared.

Interfacing Circuits

The analog front-end for the MEMS microphones comprised a non-inverting amplifier stage with 33 dB gain, which was selected such that the signals do not saturate but are amplified to utilize the full dynamic range of the subsequent analog-to-digital converter, and a high-pass 15 Hz cutoff frequency. This stage was followed by a second-order low-pass filter with a cutoff frequency of 21 kHz. A bandwidth of 15 Hz-21 kHz was chosen, as knee joint sounds can range between these frequencies.

The analog front-end for the piezoelectric film microphones comprised an amplification stage of gain 45 dB and 100 Hz high-pass cut off. This stage was followed by a fourth-order low pass filter with a 10 kHz cut-off frequency. A 100 Hz high-pass cut off was chosen to attenuate the interface and motion artifact noise.

Human Subject Study and Measurement Protocol

Thirteen male subjects without history of knee injuries participated in the study and gave written informed consent approved by the Georgia Institute of Technology Institutional Review Board (IRB) and the Army Human Research Protection Office (AHRPO). The subject population was reasonably homogenous in terms of physical activity level (collegiate athletes) and ranged in age (19-21 years), weight (84.1-135.3 kg), and height (174-195 cm). With this approach, the plan was to assess the variability in the measurements separately from variability due to age or knee joint health.

Following preliminary measures of body composition, height, and weight, an electret and MEMS microphone were both positioned at the lateral and medial sides of the subject's patella targeting the patellofemoral joint while two piezoelectric film sensors were placed on the skin just proximal and distal to the patella. Each sensor was attached using Kinesio Tex tape. In addition to the tape, a thin piece of silicone (5 mm thick) was placed over the piezoelectric film to reduce the interface noise of the tape rubbing against the film. Lastly, two wireless inertial measurement units (IMUs) (MTW-38A70G20, Xsens, Enschede, The Netherlands), which contained three-axis accelerometer, gyroscope, and magnetometer as well as built-in sensor fusion outputs, were positioned on the lateral sides of the thigh and shank.

Figure 2:
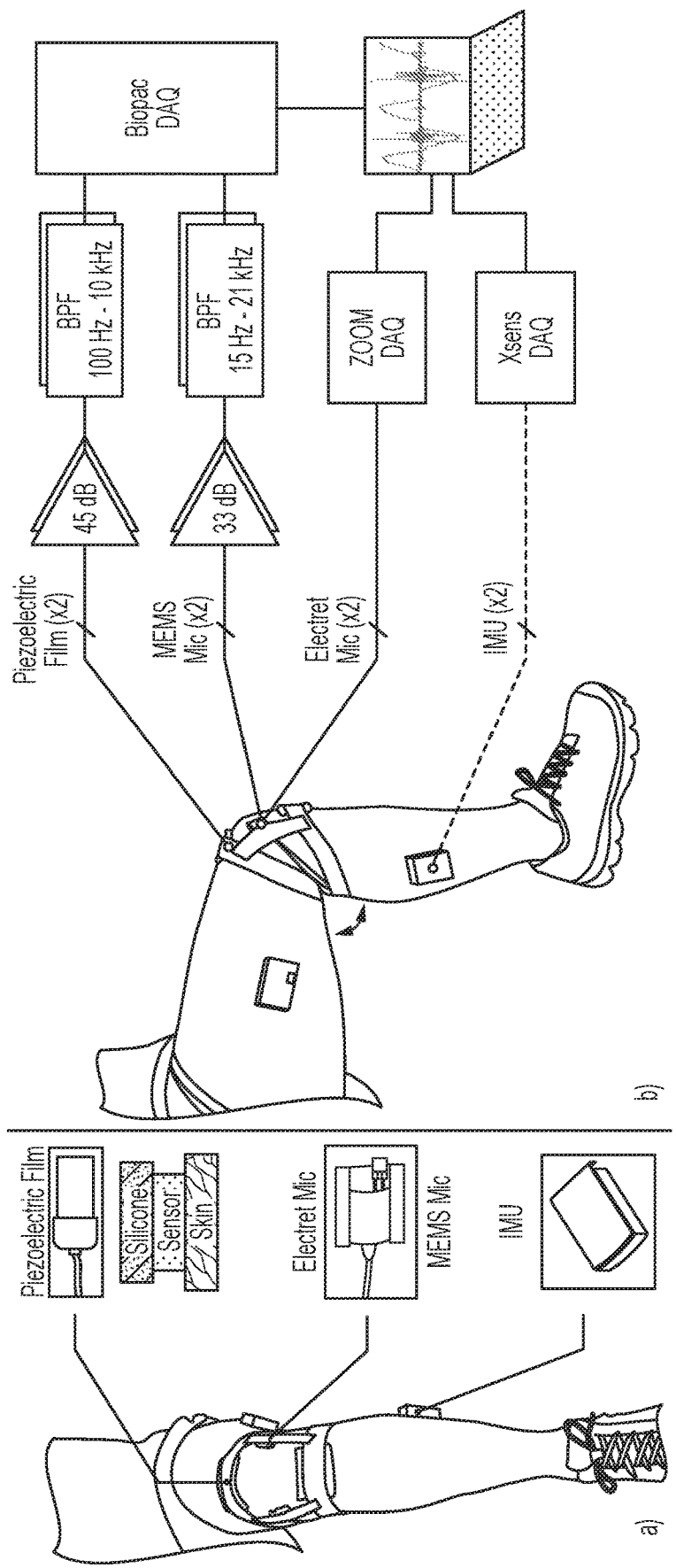
FIGS. 2(a)-(b) illustrate sensor placement and measurement block diagrams according to an exemplary embodiment of the present invention.

FIG. 2 illustrates sensor placement and measurement block diagram. In FIG. 2(a), eight sensors were used during human subject testing. Two IMUs were placed laterally on the thigh and shank. Piezoelectric film sensors were placed directly proximal and distal of the patella. The air microphones (MEMS and electret) were attached on the lateral and medial sides of the patella. FIG. 2(b) is a block diagram of the data collection hardware used during human subject studies.

While wearing these sensors, each subject completed two exercises: (i) seated, unloaded knee flexion/extension and (ii) sit-to-stand. For each exercise, the subject repeated the motion five times while the microphone and IMU outputs were recorded in a quiet room (FIG. 2(b)). The signals from the piezoelectric and MEMS microphones were passed through custom circuits and then collected at 50 kHz (16 bits/sample) using Biopac data acquisition hardware (Biopac Systems Inc, Goleta, Calif., US) while the signals from the electret microphones were sampled at 44.1 kHz (16 bits/sample) using a Zoom H6 recorder (Zoom Corp., Tokyo, Japan).

The IMU signals were acquired at 50 Hz (16 bits/sample) using their device-specific software suite (MT Maanager, Xsens, Enschede, The Netherlands) synched with the Biopac system. Apart from the electret microphone signals, which were stored on an SD card (SanDisk, Milpitas, Calif., US) via the Zoom recorder, all signals were recorded on a laptop. The data were then processed using MATLAB (The Mathworks, Natick, Mass.).

Joint Sound Processing

The signal processing comprises (i) calculation of knee joint angle and contextualization of the joint sounds with joint angle, (ii) identification of significant high frequency acoustic emissions or clicks, and (iii) statistical analysis to quantify the consistency of occurrence of the main clicks with respect to joint angle.

First, the knee joint angle was calculated using the methods that leverage the sensor fusion outputs of 3-axis accelerometer, gyroscope, and magnetometer provided by Xsens, namely the rotation matrix (i.e., Direction Cosine Matrix), and the kinematic constraints of a hinge joint to provide angle data. This method allowed for arbitrary sensor placement and orientation on each segment of the joint (i.e., thigh and shank), eliminating the need for precise calibration techniques and measures. However, this method is potentially susceptible to error, due to deviations from a true hinge joint as a result of skin and motion artifacts. Nevertheless, since the cycles of repetitive motions were analyzed against one another, this error was common to each cycle and thus did not present in the results.

Finally, the signal was normalized between 0° and 90° such that subjects could be compared against one another with respect to location within each subject's range of motion.

Figure 3:
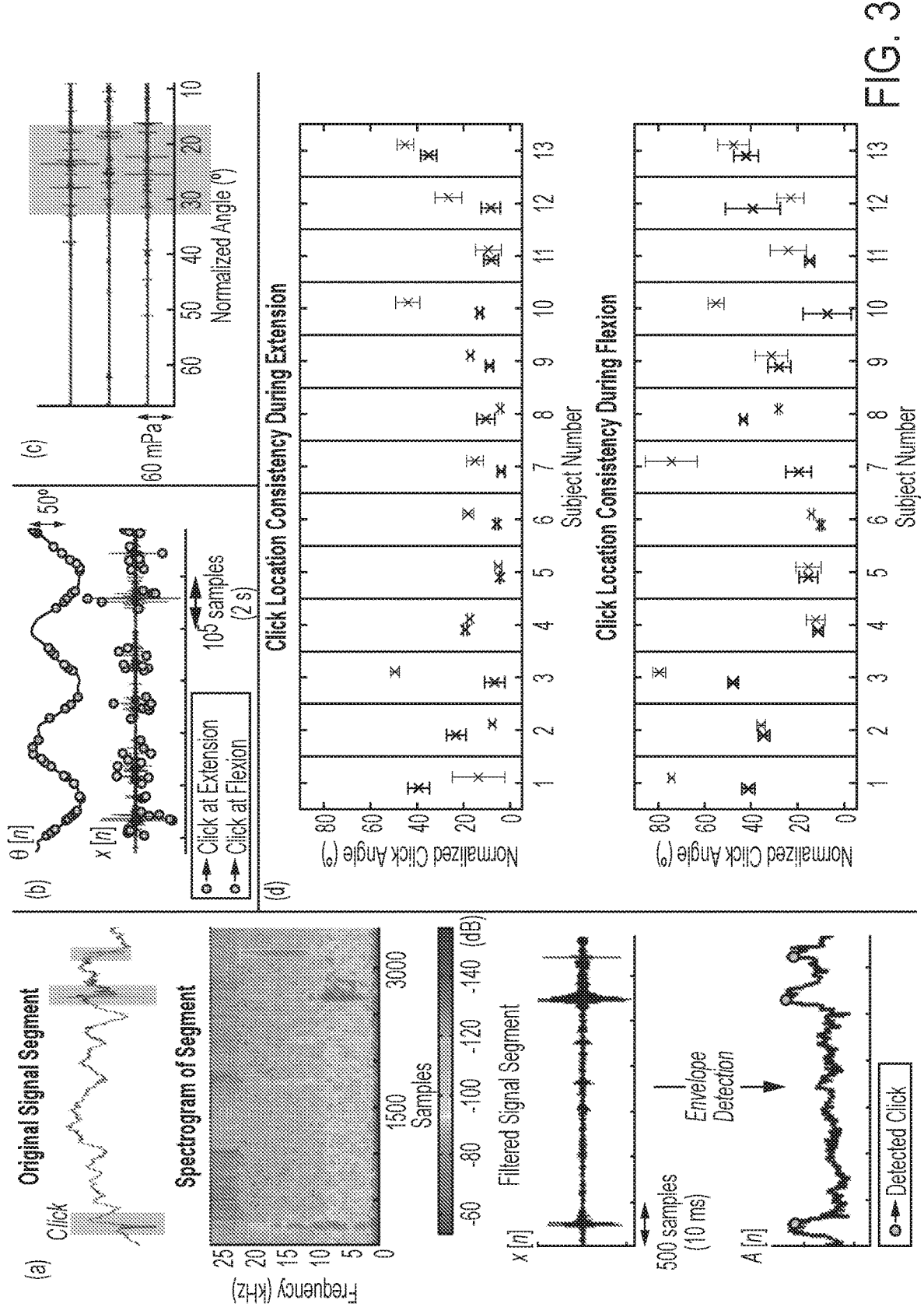
FIGS. 3(a)-(d) illustrate joint sound processing of recordings taken with an electret microphone positioned at the lateral side of the patella (a-c) and results (d) according to an exemplary embodiment of the present invention.

FIGS. 3(a)-(d) illustrate joint sound processing of recordings taken with an electret microphone positioned at the lateral side of the patella (a-c) and results (d). FIG. 3(a) is an example 3000 sample (60 ms) joint sound recording window showing three distinct high-amplitude, short-duration, acoustic emissions. The original signal contains ambient noise, which presents as broadband signals up to 7 kHz, and interface noise, which appears as baseline movement. These components are clearly visualized in the spectrogram of the original signal. To remove the majority of the noise, the signal is bandpass filtered at 7 kHz-16 kHz, resulting in the filtered signal x[n].

The envelope of this signal is found, yielding A[n]. Using a thresholding technique based on the moving average, the significant peaks of A[n] are found, roughly corresponding to the clicks of the original signal. These are later refined to match the true locations of the clicks found in the original signal (i.e., such that the locations correspond to where the clicks achieve their maximum amplitudes, positive or negative, in the original signal). FIG. 3(b) illustrates a final result of the click detection algorithm, which displays the identified clicks for three cycles of flexion/extension. FIG. 3(c) illustrates three extension cycles with artificial offsets. These qualitatively show that the main acoustic event of each cycle occurs at similar angular locations. FIG. 3(d) illustrates the final results of click location consistency for five repetitions of flexion/extension for 13 subjects on left and right legs. Across subjects, the standard deviation for click location is small, supporting observations of consistent angular location cycle-to-cycle. Additionally, the mean locations of these clicks are consistent between left and right legs for most of the subjects.

As discussed and in more detail, once knee joint angle was calculated, the phases (flexion or extension) of each cycle were determined (FIG. 3(b)). First, the inflection points of the signal were found. The beginning and ending of each phase were identified by finding pairs of inflection points. These points were then used to segment the microphone signals, contextualizing the data by type of angular motion.

Next, significant acoustic emissions were identified. The most distinct audio signals that were detected by the air microphones were the high amplitude, short duration clicks (FIG. 3(a)). By observing the signal's frequency content (i.e., short-time Fourier transform, STFT), these clicks were broadband with frequencies as high as 20 kHz. This unfiltered signal contained two main sources of noise; ambient noise ranged in frequency up to 7 kHz while interface noise appeared as baseline movement with components up to 1.5 kHz. The first step of this identification stage was to preprocess the signal such that the clicks became more prominent and any interface and/or ambient noise were mostly cancelled. To this extent, the air microphone signals were filtered with a bandpass filter spanning 7 kHz-16 kHz. As seen from FIG. 3(a), the filtered signal (x[n]) lacks the original baseline movement, and the clicks are more distinct from other artifacts in the signal.

After this preprocessing step was complete, a modified envelope detection algorithm was implemented. A 1024-bin spectrogram of the signal (X[n, m]) was calculated with a window size of 100 samples (i.e., 2 ms) and 90% overlap. The amplitude of the signal was calculated by summing the logarithmic amplitude of the spectrogram across the frequency bins as follows:

$$A[n] = \sum_j 20\log|X[n, j]| \quad (1)$$

A moving average and standard deviation ($\mu[n]$ and $\sigma[n]$) of A[n] using a window size of 1000 samples was calculated. A[n] was then thresholded such that:

$$T[n] = \begin{cases} A[n], & A[n] > \mu[n] + \alpha \cdot \sigma[n] \\ 0, & \text{otherwise} \end{cases} \quad (2)$$

where T[n] is the thresholded amplitude signal and a is a constant control coefficient, which was selected as 3.3 by inspection.

Next, the peaks of T[n] were detected by standard peak detection techniques. The peaks that resulted from the same click (i.e., resonances of the initial click, which are specified as peaks within 150 samples of each other) were eliminated, resulting in the raw click locations vector $p_r=[p_{r1}, p_{r2}, \ldots, p_{rL}]$. The raw click locations $P_r$ were refined such that each click location corresponded to the point on the original filtered signal where the click achieved its maximum amplitude, positive or negative. The refined click locations matrix $p=[p_1,p_2, \ldots, p_L]$ gave the final detected click locations. An example of these detected clicks is shown in FIG. 3(b).

Once the clicks were identified, the consistency of these acoustic emissions was analyzed. FIG. 3(c) provides a visualization of consistent acoustic emission during repetitive motion. For each cycle of a particular exercise (i.e., flexion or extension), the three clicks with the largest amplitudes and their corresponding angular locations were determined. Each combination of the clicks across cycles (i.e., selection of one of the three clicks from each cycle) was found. The combination with the smallest standard deviation for angular location yielded the most consistently occurring major acoustic event. The mean and standard deviation of these locations were calculated.

Given these mean locations, three methods were used to analyze the data. For the first two methods, test-retest reliability was estimated using the ICC. The data was organized into "motions" and "repetitions." There were 52 "motions," one for each human subject and exercise combination (e.g., subject 1's extension data represented one "motion"). The "repetitions" comprises the five click locations (one per cycle) from the selected combination. This dataset will be referred to as the test-retest dataset.

Given this dataset, two ICC values were calculated using one-way random single (i.e., ICC(1, 1)) and average measure (i.e., ICC(1, k)) models to show the reliability of a single cycle's measure and mean of the fives cycles' measures. Additionally, the 95% confidence intervals (CI) for these two ICC values were determined. The last method for analyzing the data was a paired t-test, which was used to assess whether there were significant differences between the mean click locations for left and right legs.

Results And Discussion

Microphone Comparison

In evaluating microphone selection, many different parameters were considered. First, the similarity of the signals measured by the electret and MEMS microphones were compared. The quality of these microphones was determined by evaluating the quality of their sensing capabilities in terms of SNIR. Moreover, when investigating interface issues for the air microphones, the effect that the sensor-to-knee distance had on the signal acquired was examined. Finally, the quality of the contact microphone was researched.

Figure 4:
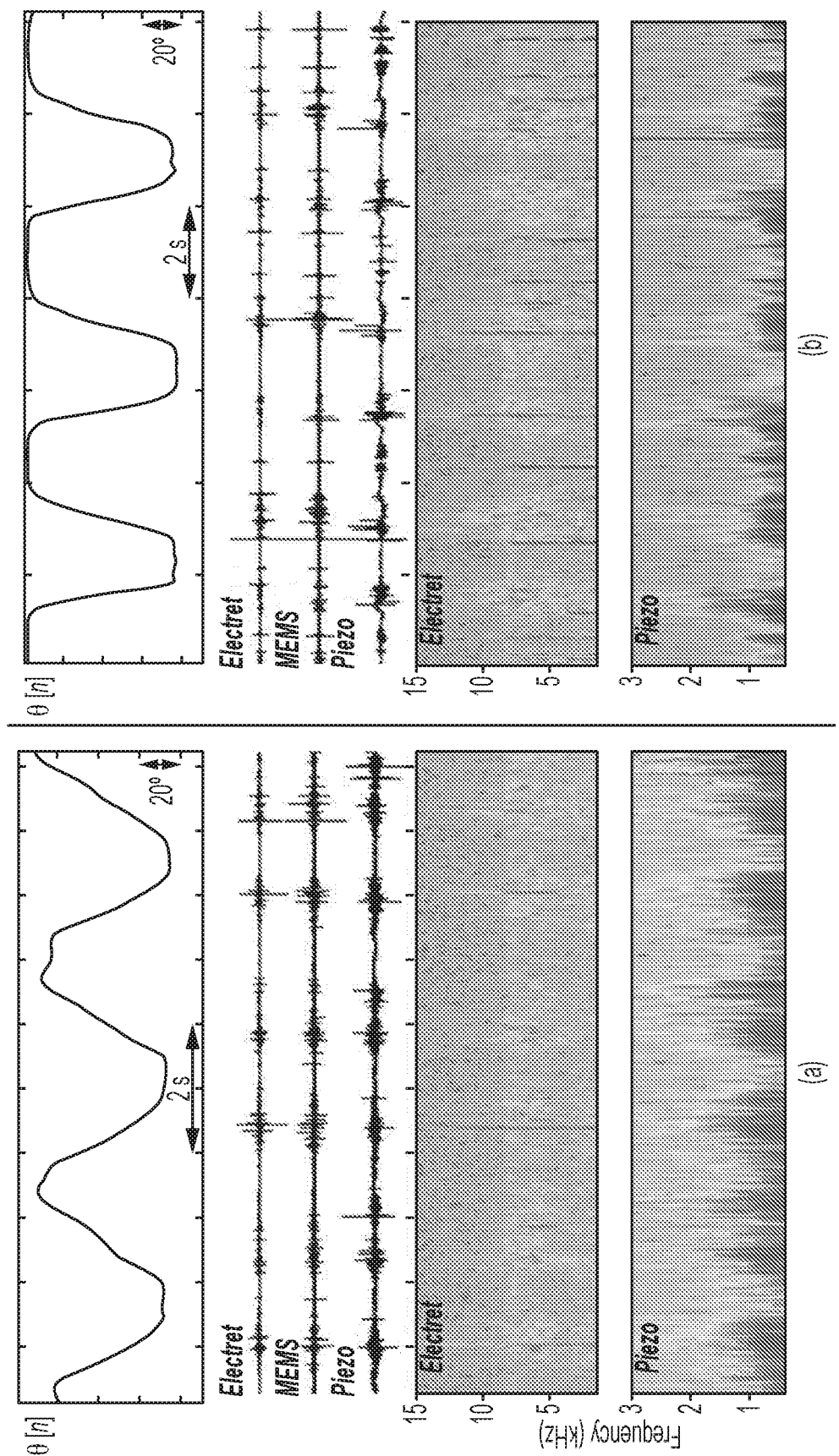
FIGS. 4(a)-(b) illustrate joint sounds simultaneously sensed by electret, MEMS, and piezoelectric film microphones during three repetitions of (a) flexion/extension and (b) sit-to-stand exercises according to an exemplary embodiment of the present invention.

FIG. 4. illustrates joint sounds simultaneously sensed by electret, MEMS, and piezoelectric film microphones during three repetitions of FIG. 4(a) flexion/extension and FIG. 4(b) sit-to-stand exercises. For both parts FIGS. 4(a)-(b), the top plot displays the joint angle ($\theta[n]$). The middle and bottom graphs show the time and frequency domain signals from the various microphones. The acoustic signatures of the electret and MEMS microphones exhibit similar characteristics.

As shown in FIGS. 4(a)-(b), the electret and MEMS microphones, measuring frequencies as high as 20 kHz, performed similarly in detecting joint sounds, which were acquired from a subject performing flexion/extension and sit-to-stand exercises respectively. This was confirmed by computing the information radius between the normalized histograms of signals captured by these two microphones, which yielded a value of 0.0025. This value shows a high similarity between these two types of microphones since the information radius ranges from 0 for identical distributions to 2 for maximally different distributions. This shows that the more cost-effective MEMS microphones are a viable substitute for the more expensive electret microphones. This is an important result when designing deployable systems.

As predicted, the signal recorded by the air microphones included noise and interface components in addition to the desired joint sounds; both ambient background interference and interface noise caused by the rubbing of athletic tape, which was used to hold the sensors in place, were sensed by the microphones. The SNIR was 11.7 dB for the electret microphone and 12.4 dB for the MEMS microphone. To minimize issues with noise during initial experiments, measurements were taken in a quiet room. Further investigation can be addressed for implementation of a deployable, wearable system, especially given the fact that many background noises, such as speech and sounds due to ambulatory motion, will reside in-band with the joint sounds.

Figure 5:
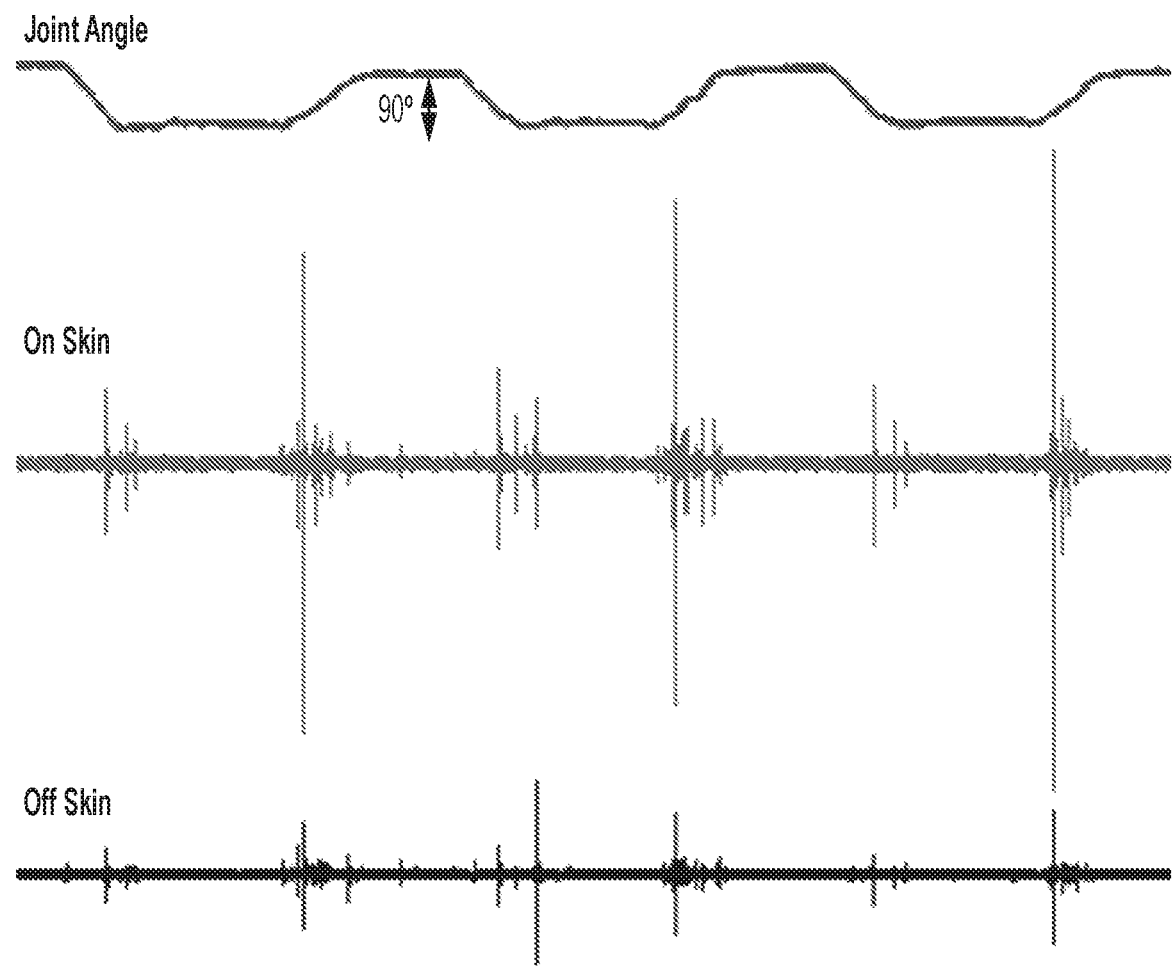
FIG. 5 illustrates joint sounds measured on the skin and 5 cm off the skin during flexion/extension exercises according to an exemplary embodiment of the present invention.

FIG. 5 illustrates joint sounds measured on the skin and 5 cm off the skin during flexion/extension exercises. Though the off-skin microphone captured a signal with decreased amplitude, the on-and off-skin measurements showed significant similarities in their acoustic signatures. The main acoustic event of each signal occurred at similar locations.

Experiments showed that the air microphones did not need to be directly located at the skin surface to detect airborne joint sounds. As shown in FIG. 5, the sounds obtained from an electret microphone placed on the skin and one located 5 cm off the skin captured similar acoustic signals in both morphology and timing (~4.5× smaller amplitude). This is an important observation because it suggests that the air microphones can record joint sounds in a wearable device where direct contact with the skin may not be constant. However, it will be important to consider this distance when analyzing the captured signals, particularly when the analysis depends on the amplitude of the signal.

In this sense, maintaining a fixed distance between the microphone and skin, especially for use in longitudinal analysis, may be required. Furthermore, placing the microphone off of the skin introduces increased potential for noise; the microphone may have a greater opportunity to strike or rub against the skin. Additionally, changing the distance between the microphone and skin will change the microphone's sensitivity in sensing these sounds.

The piezoelectric film measured signals up to approximately 3 kHz as seen from the spectrograms of the signals acquired shown in FIG. 4. While the piezoelectric film had the advantage of not detecting background noise, it acquired significantly more interface noise-8.4 dB SNIR-due to the sensor rubbing on the skin and the athletic tape rubbing on both the skin and the sensor. This interface noise had frequency components up to 1.5 kHz and was thus in-band.

During early pilot data collections, the piezoelectric film was attached to the skin using only Kinesio Tex tape. However, this method proved to be very susceptible to interface noise. As the knee extends and flexes, the tape, though stretchable, deformed the film which obscured the low frequency and low amplitude signatures. Furthermore, though acceptable for collecting pilot data, tape proves to be undesirable for long-term monitoring. To mitigate this issue, a piece of silicone was placed above the piezoelectric film. Because silicone has similar compliant mechanical properties to skin and subcutaneous tissue, the joint sounds received did not experience dampening, and the silicone surface provided a suitable surface to stick the tape. Though this method did not completely eliminate interface noise-the sensor still experienced some movement along the skin-it did help to reduce the recorded noise.

Accordingly, while using piezoelectric film or other contact microphones is desired to capture the vibration signal, which represents the majority of the acoustical energy generated, implementation presents practical issues. The piezoelectric film was significantly affected by interface noise. A smaller portion of the signal bandwidth was corrupted by interface noise for the air microphones compared to contact microphones. Furthermore, contact microphones did not pick up higher frequency vibrations as distinctly as air microphones. For these reasons, the use of air microphones for wearable joint sound measurements might be preferable.

Joint Sound Consistency

FIG. 3(d) summarizes the results for mean angular click location for the left and right legs of 13 seated subjects performing five repetitions of knee flexion/extension. Two important findings resulted from this data: (i) significant acoustic events are repeatable during single trial measures, and (ii) left and right legs produce similar sounds.

First, two ICC values were found for the test-retest dataset. An ICC(1,1) value of 0.94 with a 95% CI of 0.92-0.97 and an ICC(1, k) value of 0.99 with a 95% CI of 0. 98-0.99 were calculated. Since the ICC values were greater than 0.7, these values showed that the main acoustic emission per cycle of activity were consistent within a single trial of monitoring for both single and average measure reliability. Given that audible joint sounds have not been extensively explored, this was an important finding, demonstrating that airborne signals emit a stable pattern with repeated movement in a healthy hinge joint.

Second, the difference between legs for each exercise suggested that a healthy subject's knees produce similar joint sounds. The difference between left and right legs were not significant at the $p<0.05$ level. While as a group, there were no significant differences between the left and right legs, some subjects could be grouped as having relatively no difference between right limb and left limb click locations whereas others had notable differences between right and left suggesting the potential for defining clinically relevant "signature traits". Such variations in click location could represent useful knee joint health biomarkers.

Though these results are promising, there are some limitations to the tested system and analysis. First, with regard to the IMUs, sensor positioning, drift, and motion artifacts can all contribute to flexion angle calculations that differ from the true joint angle. Techniques discussed herein and others will need to be employed to minimize these errors, especially when considering their application in a system which measures longitudinal data. For example, some errors could be minimized by ensuring more rigid sensor positioning and leveraging the joint's kinematic constraints directly into the calculation of joint angle to reduce the effect of drift.

Second, the effect of lubrication (e.g., diminished boundary lubrication after an injury) and differing structural components (e.g., damaged ligaments, etc.) on acoustic emissions has not yet been sufficiently studied. These variables may introduce "error" when calculating click location consistency for repeated cycles and measuring differences between legs. In this sense, these isolated, one-time measurements may not prove to be as useful as compared to longitudinal analysis for the same subject over time.

These quantitative findings in terms of measurement consistency form the foundation for understanding the significance of changes in joint sound signatures associated with injury, as well as changes in such signatures during rehabilitation. Moreover, while longitudinal studies will be important towards understanding injury recovery, this work and its focus on robust implementation in a wearable platform also presents opportunities for exploring day-to-day and within-day changes of joint acoustics.

CONCLUSIONS

In an exemplary embodiment of the present invention, wherein the multi-modal sensing relates to knee joint acoustic emission during loaded and unloaded activities, it is demonstrated, quantitatively, that major acoustic events occur at consistent joint angles during repetitive motions for healthy subjects. Furthermore, these locations are similar between left and right legs for most subjects. Whether asymmetry between right and left knee acoustic emissions is related to risk factors for injury or other training-related variables remains to be clarified. Importantly, these findings showed that joint sound measurements from air microphones are repeatable with sensing technology that can be implemented in a relatively inexpensive, wearable form factor. While extensive analysis of the piezoelectric film was not conducted, its use in a wearable device holds promise based on preliminary findings showing that packaging techniques have a large influence on the signal recorded.

The present invention further includes mitigating background and interface noise for both the air and contact microphones. In particular, a focus on the packaging of these sensors into a wearable wrap or sleeve enabling high quality signal measurements during at-home, long-term monitoring is investigated. Additionally, existing algorithms are refined and new processing techniques developed to detect clinically-relevant acoustic signatures.

Given that therapists and clinicians look at sounds, swelling, structural stability, and range of motion, the present invention investigates methods for quantifying these joint health biomarkers unobtrusively and accurately; namely, it determines which acoustic signatures encapsulate these biomarkers. Furthermore, exploration of these biomarkers as they relate to specific diseases and injuries (e.g., osteoarthritis, anterior cruciate ligament tear, meniscal tear, etc.) are considered. Finally, longitudinal studies on injured subjects allow for the determination and validation of specifics acoustic emission features (e.g., consistent angular location) that provide valuable joint health information during rehabilitation following an acute injury.

A Robust System for Longitudinal Knee Joint Edema and Blood Flow Assessment Based on Vector Bioimpedance Measurements In another exemplary embodiment of the present invention, joint characteristics including edema and blood flow parameters are examined and systems and methods of wearable joint rehabilitation assessment following musculoskeletal injury using bioimpedance technologies readily integrated into a wearable device.

In this embodiment of the present invention, systems and methods are disclosed that address technological gap in the area of wearable bioimpedance measurement systems for local joint physiology assessment.

Position Identification Algorithm

Bioimpedance measurements are too greatly impacted by motion artifacts, subject position, electromagnetic interference and voltage fluctuations of the skin electrode interference. Therefore for consistency, measurements should be taken when subject is still in a given position and in the absence of electromagnetic interference and skin electrode interface related fluctuations (such as an electrode loosing contact with the skin). These conditions can be met under user guidance however this kind of guidance is not feasible in a wearable device setting.

As discussed previously, IMUs can be used to decide if the user is still and in an acceptable position for measurements to be taken. However, IMUs will not be effective in detecting electromagnetic interference or skin-electrode interface related fluctuations. These kinds of effects can however be detected using the dynamic resistance signal which is greatly influenced by them, as well as the user position and motion artifacts.

IMUs along with the dynamic resistance (impedance plethysmography) signals can be used together to decide if the user is in an acceptable position for bioimpedance measurements to be taken or not. The IMUs would be used to provide information about the subject's limb position (such as knee angle) and the activity that the subject is performing (such as walking, running, sitting still etc.). The dynamic resistance signal can be used to assist in detecting the subject's limb position and the activity being performed. It can also be used to deduce if any of the electrodes were misplaced and if any of the electrodes lost contact with the skin. If any changes on the electrode positioning occur, these can be detected through features extracted from the dynamic resistance signal. The bioimpedance measurements also get affected by muscle contractions. The dynamic resistance signal can also be used to deduce if the limb muscles are relaxed or contracted.

The dynamic resistance signal was used to design an exemplary algorithm that can decide if the user is in an acceptable position for bioimpedance measurements to be taken. IMUs can be used to assist such an algorithm as well. In this exemplary embodiment, only the dynamic resistance signal was used. In this case, the acceptable position was when the subject is motionless, seated with legs fully extended and supported from the bottom. All other positions or activities (sitting legs bent, standing, any kind of motion) were to be marked as rejected measurements. The static impedance measurements were not used in the decision process as these are the measurements to be interpreted and using them in the decision process would create tendency to acquire data within a certain range of values.

Figure 6:
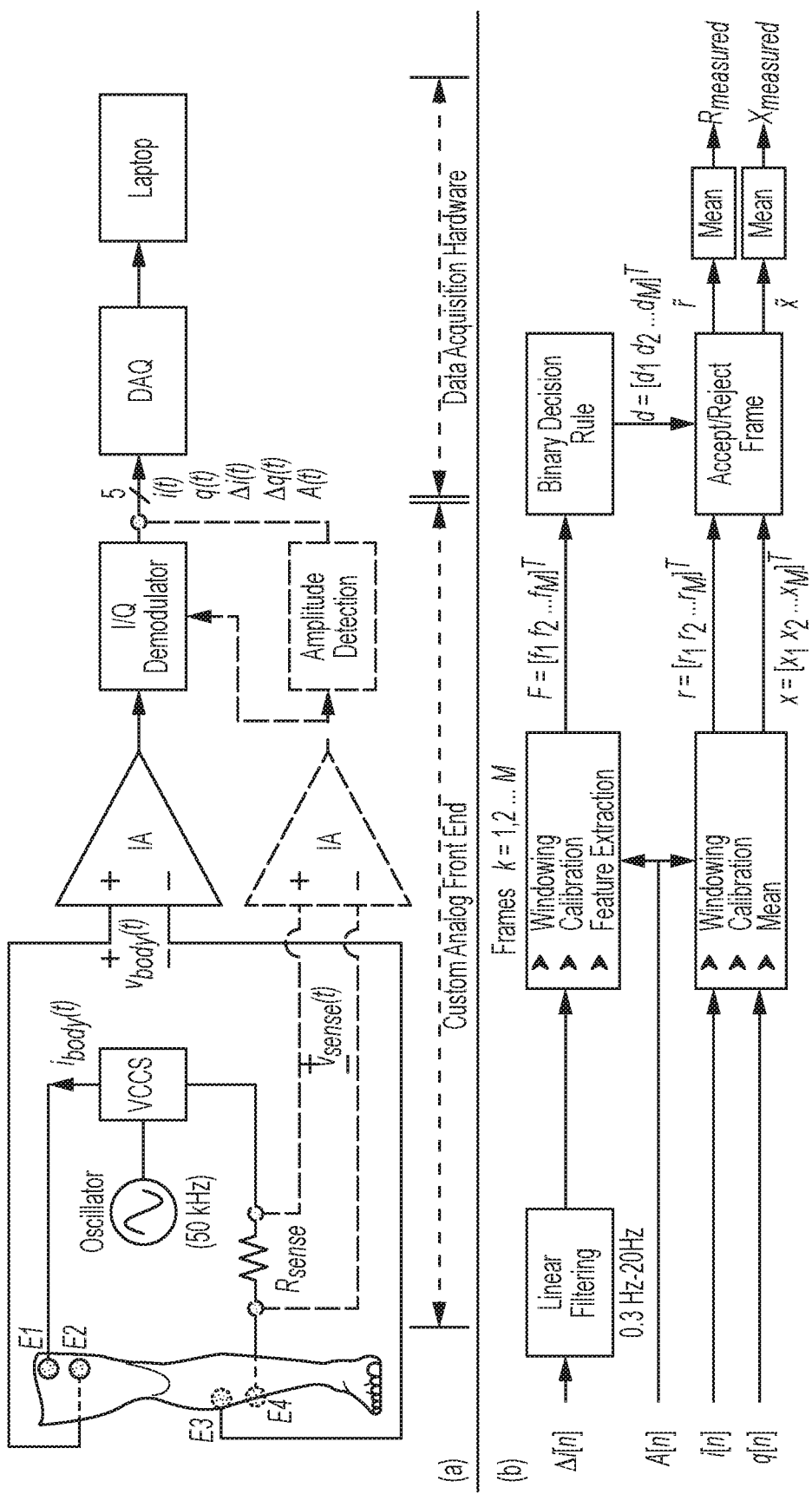
FIG. 6(a) is a block diagram of a bioimpedance measurement system according to an exemplary embodiment of the present invention.
FIG. 6(b) is an algorithm for identifying the time intervals when the user is in the correct position to acquire measurements (sitting, legs extended and supported) according to an exemplary embodiment of the present invention.

FIG. 6(a) is a block diagram of a bioimpedance measurement system according to an exemplary embodiment of the present invention. E1-E4 represent the electrodes that interface to the body. The signals i(t) and q(t) relate to the static (slowly varying on the order of hours to days) component and the signals) $\Delta i(t)$ and $\Delta q(t)$ relate to the dynamic component of the knee impedance. A(t) is used to monitor the amplitude of the current i ($i_{body}(t)$ passing through the knee joint.

The position identification algorithm is summarized in FIG. 6(b) and used for identifying the time intervals when the user is in the correct position to acquire measurements (sitting, legs extended and supported). The acceptable time intervals are identified by extracting features from the dynamic voltage signal $\Delta i[n]$ and using these features to make a decision. The binary decision rule is trained once before-hand. The accepted time intervals are used to obtain the knee resistance ($R_{measured}$) and reactance ($X_{measured}$) using the static voltage measurements i[n] and q[n]. A[n] is used to cancel the effects of any variations in injected current amplitude.

The signal $\Delta i[n]$ is linearly filtered (0.3 Hz-20 Hz) to get rid of respiratory artifacts and high frequency noise. Then, the filtered signal is windowed with a window size of 10 seconds and a step size of 1 second (decided heuristically)

creating M frames of the filtered signal. The signal in each frame is amplitude corrected using A[n] and calibrated to give the dynamic resistance signal within the frame.

Features extracted from each frame are placed in a feature matrix $F=[f_1 f_2 \ldots f_M]^T$, where each column corresponds to a feature and each row to a frame. These features are then used to decide whether a frame should be accepted (classified with label 1 or rejected classified as 0), producing a vector of binary labels $d=[d_1 d_2 \ldots d_M]^T$. Frames with standard deviation of the dynamic resistance signal exceeding 50 m$\Omega$ are labeled 0 because it is highly likely they contain motion.

The static voltage measurements i[n] and q[n] are also windowed using the same scheme, amplitude corrected using A[n] and calibrated producing the resistance and reactance signals for each of the M frames. The mean of the resistance and reactance signals for each frame are taken to give the average resistance and average reactance vectors, $r=[r_1 r_2 \ldots r_M]^T$ and $x=[x_1 x_2 \ldots x_M]^T$ respectively. These M resistance and reactance measurements are either accepted or rejected according to the labels in vector d. The accepted resistance and reactance measurements are placed into the accepted resistance ($\tilde{r}$) and accepted reactance ($\tilde{x}$) vectors respectively. The mean of $\tilde{r}$ and $\tilde{x}$ are taken to give the final measured resistance ($R_{measured}$) and reactance ($X_{measured}$).

The binary decision rule mentioned is trained separately before it is applied to new data (a testing set). For this training, $\Delta i[n]$ is recorded while the subject does activities with known labels for a known amount of time: (1) standing (label 0), (2) sitting legs bent (label 0), (3) sitting legs crossed (label 0), (4) sitting legs extended and supported (label 1) and (5) walking (label 0) each for 1 minute.

Feature extraction is performed on $\Delta i[n]$ as shown in FIG. 6(b) to produce a feature vector $F_{training}$ and the corresponding known labels $d_{training}$. Feature subset selection is performed on the features in $F_{training}$ via classifier subset evaluation using a support vector machine (SVM) classifier with a genetic search algorithm. The selected subset of features and $d_{training}$ are used to train an SVM (with a cost parameter of 1.0) resulting in the binary decision rule to be used. Note that $F_{training}$ and $d_{training}$ do not include those frames where the standard deviation of the dynamic resistance signal exceeds 50 m$\Omega$ (frames with motion artifacts). The feature subset selection and SVM training were carried out using Weka while all other tasks were done on MATLAB.

The features extracted from each frame are described in three categories. The first category of features is generic features that were derived from audio signal feature extraction techniques. The 10-second frame is further partitioned into sub-frames of size 700 ms with 350 ms step size. Temporal and FFT related features (30 features) are extracted from each 700 ms sub-frame, these are the short-term features. Statistics also referred to as mid-term statistics, such as mean, median and standard deviation (8 statistics) are computed for each feature across all the 700 ms sub-frames resulting in a total of 240 features per frame.

The second set of features is based on the frequency content of the ensemble average of the dynamic resistance waveform across each frame (4 features). The ensemble average of the waveform across the frame is computed using an algorithm. The last sets of features are temporal features extracted from the ensemble average dynamic resistance signal for each frame (23 features).

Figure 7:
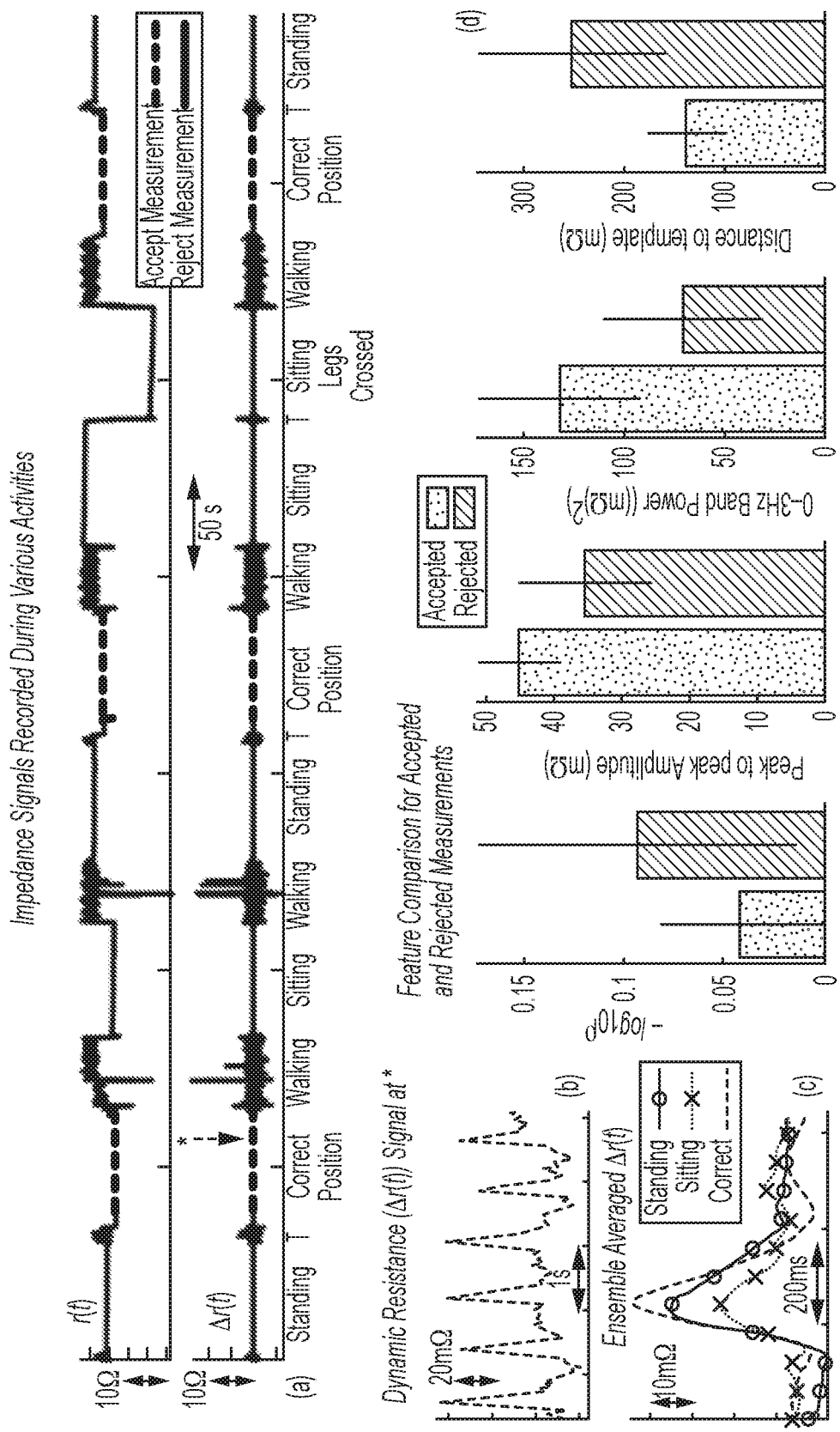
FIG. 7(a) show static and dynamic resistance signals (r(t) and Δr(t)) measured from a subject during various activities according to an exemplary embodiment of the present invention.
FIG. 7(b) is a segment of the dynamic resistance signal, zoomed in at * (see FIG. 7(a)).
FIG. 7(c) is an ensemble averaged dynamic resistance signals while the subject assumes different positions.
FIG. 7(d) illustrates the means and the standard deviations of four features extracted from Δr(t) shown in bar graphs for the accepted and rejected measurement time intervals.

FIG. 7(a) show static and dynamic resistance signals (r(t) and $\Delta r(t)$) measured from a subject during various activities. The time intervals marked when the subject is in the correct position for taking measurements (sitting, legs extended and supported). The measurements taken when the subject is in the correct position are to be accepted, all other measurements should be rejected. The position identification algorithm is tested on this data. FIG. 7(b) is a segment of the dynamic resistance signal, zoomed in at * (see FIG. 7(a)). The pulsatile component of the signal due to blood flow is clearly seen. The characteristics of this signal are used for position identification.

FIG. 7(c) is an ensemble averaged dynamic resistance signals while the subject assumes different positions. Each ensemble average was taken over a time interval of 40 seconds. The difference in the ensemble average waveforms as the subject assumes different positions can be seen clearly. FIG. 7(d) illustrates the means and the standard deviations of four features extracted from $\Delta r(t)$ shown in bar graphs for the accepted and rejected measurement time intervals. The first graph shows the bar graph for ($-\log_{10} \rho$) which is related to the SNR of the signal. The second graph is for the peak to peak amplitude of the ensemble average of the signal. The third graph is the 0-3 Hz band power of the ensemble averaged signal. The final graph is for the Euclidean distance between the ensemble average waveform and a template ensemble average waveform acquired during the one-time training phase while the subject assumes the correct position.

The static and dynamic resistance signals measured, while a subject performs a variety of activities is shown in FIG. 7(a). The time intervals where the subject is in the correct position (seated, legs extended and supported) for the measurement to be acceptable are shown in red, while all others are shown in black: subject standing, seated with legs bent 90°, seated leg crossed, walking). This measurement was made over a course of 12 minutes. It can be seen from this figure that both the dynamic and static resistances are greatly impacted by motion artifacts (transition motion labeled as T, walking), which create variations in the orders of one to tens of Ohms.

A portion of the dynamic resistance waveform while the subject is in the correct position is shown in FIG. 7(b). While the subject is still, this waveform varies periodically over the course of milliseconds, and the variability is in the order of tens of miliOhms. The static components of the signal do not have this periodic variability as it has been filtered out.

The ensemble averaged dynamic resistance waveforms for three 80-second time intervals where the subject was in different positions (standing, seated legs bent 90°, correct position) are shown in FIG. 7(c). This figure points out some features that can be effective in classifying the time intervals with the correct position from the others, such as the peak to peak amplitude of the ensemble averaged $\Delta r(t)$ waveform. It can also be seen that the correct position's waveform looks smoother (and thus less noisy) than both the standing and the sitting position's waveforms. This suggests that features related to the SNR, frequency domain and shape of the ensemble averaged $\Delta r(t)$ waveform are potentially effective features as well.

FIG. 7(d) shows the means and standard deviations of four features extracted from the 10 s time windows where the subject is in the correct position (accepted measurement windows) and incorrect position (rejected measurement windows) for the 12 minute measurement shown in FIG. 7(a). The first feature (shown on the leftmost bar graph) is the minus logarithm of the cross-correlation coefficient between the even and odd sub-averages ($-\log_{10} \rho$) within the 10 second frame. This feature is inversely related to the SNR of the ensemble average waveform. The second and third features (second and third bar graphs from the left) are the peak to peak amplitude and the 0-8 Hz bandpower of the ensemble averaged Δr(t) waveform within each 10 second frame. The final feature shown (the rightmost bar graph) is the Euclidean distance between the ensemble averaged Δr(t) waveform, and a template ensemble averaged Δr(t) waveform taken during the training phase while the subject was in the current position.

As predicted from FIG. 7(c), these four features show effective class separability. Lilliefors and Kolmogorov-Smirnov tests performed on each class and each of the features showed that the distributions were normal (p<0.01). A two-sample t-test (with unequal and unknown class variances assumed) showed significant class separability in each feature (p<0.01).

The training data was used to train a binary classification rule using the method described above. The confusion matrix for the classifier evaluated on the testing data where frames with motion (standard deviation of Δr(t)>50 mΩ) are not included is seen on TABLE I.

TABLE I

Confusion Matrix for the Position Identification Algorithm Evaluated on the Testing Data

| N = 405 | Predicted Reject (0) | Predicted Accept (1) |
|---|---|---|
| Actual Reject (0) | 261 | 5 |
| Actual Accept (1) | 60 | 79 |

The baseline misclassification rate (when the most probable class is always chosen, reject (0) all the frames in this case) was 34.3%. The misclassification rate of the trained classifier was 16% and the precision was 94%. Therefore although a significant amount of frames that should be accepted are rejected by the algorithm, most frames accepted are actually acceptable, which is what matters the most for measurement consistency. The significant amount of false negatives is not important as the system only aims to take 5 to 10 measurements (with a 10 second duration) within a day, which makes missing some measurements non-critical. Infrequent measurements are sufficient to monitor knee joint health as the static knee impedance has physiology related variations in the course of ours to days.

Over the course of 12 minutes of testing when only the actual acceptable frames were used for the binary decision rule, the measured resistance ($R_{actual}$ or mean ($\bar{r}$) along with std ($\tilde{r}$)) was 60.9±0.6Ω and the measured reactance was −13.5±0.7Ω. The impedance measurements when all frames without motion were accepted were 60.5±4.8Ω and −13.1±1.5Ω. The higher standard deviation in the impedance measurements is due to inconsistent measurement positions.

When the binary decision rule trained was used, the impedance measurements were 60.8±1.5Ω and −13.54±1.0Ω for resistance and reactance respectively. These values are more consistent (have lower standard deviation) and have lower absolute error compared to accepting every frame without motion, due to more consistent subject positioning.

These results are a demonstration of how an algorithm can be used to automatically decide to take bioimpedance measurements when the subject is in a certain position, eliminating the need for user guidance. An algorithm requiring a one-time training similar to this can be implemented on a smart phone that wirelessly communicates with the bioimpedance hardware, which is a step towards creating a "Smart Brace" monitoring knee impedance.

Bioimpedance Systems and Methods

A system that measures bioimpedance signals and then extracts both musculoskeletal (tissue resistance and reactance), and cardiovascular (heart rate, local blood volume, and flow rate) parameters (FIG. 8) is disclosed.

Figure 8:
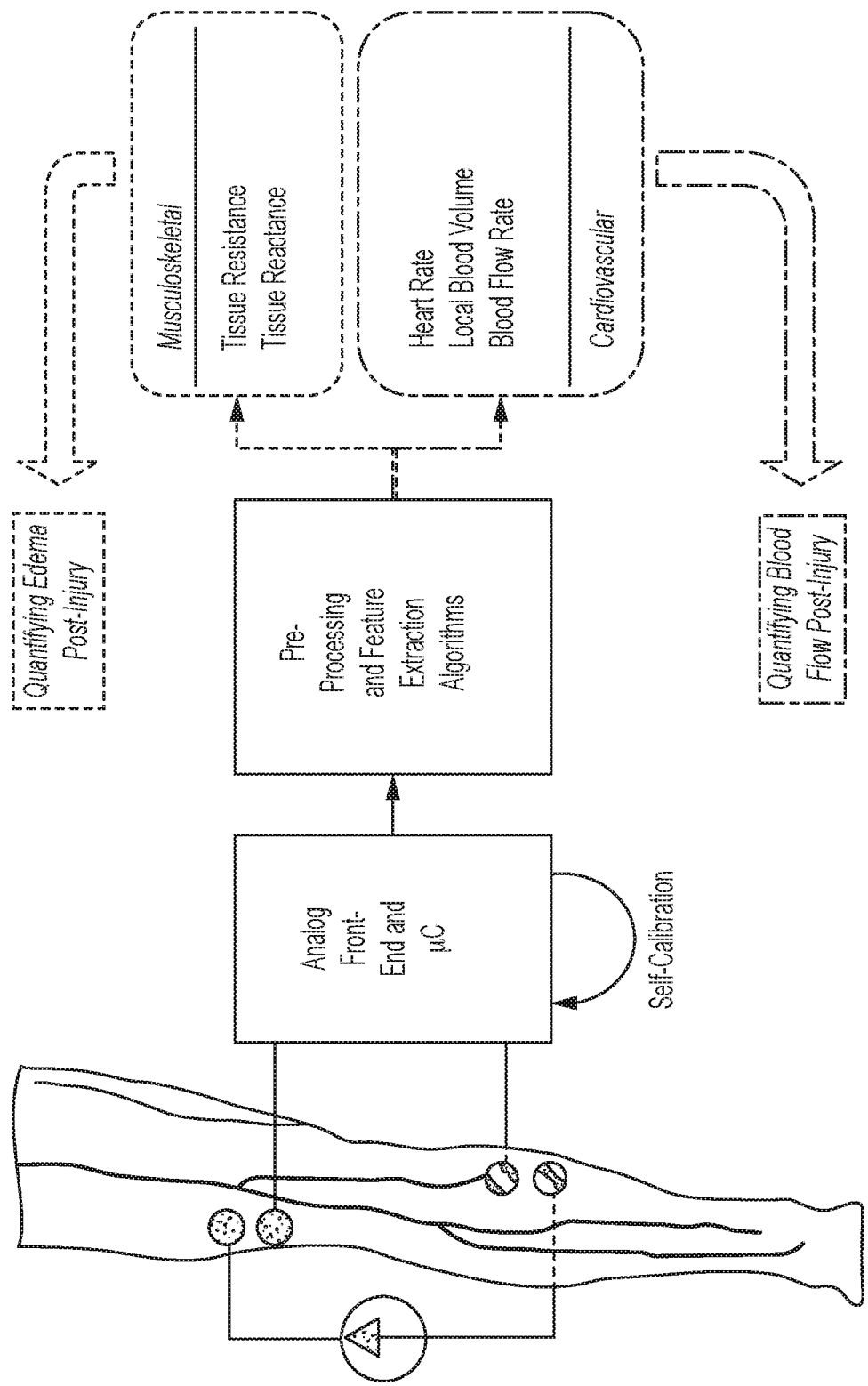
FIG. 8 is a block diagram of the bioimpedance measurement system for local joint health assessment according to an exemplary embodiment of the present invention.

FIG. 8 is a block diagram of the bioimpedance measurement system for local joint health assessment according to an exemplary embodiment. An innovative combination of both musculoskeletal and cardiovascular parameters will be obtained from the knee joint longitudinally during recovery from acute musculoskeletal injury with a wearable device based on the high performance circuit and system described here.

These physiological parameters are used to quantify both edema and blood flow during post-injury recovery. The invention advances the state-of-the-art for bioimpedance measurement systems by, among other things, (i) incorporating a custom bioimpedance measurement analog front-end for both tissue impedance (static) and local hemodynamics (dynamic) with the highest resolution given the power consumption and size, compared to similar systems, and/or (ii) employing a self-calibration procedure to minimize drift and inaccuracy due to environmental factors such as temperature, and/or (iii) creating customized physiology-driven algorithms for IPG-based heartbeat detection to alleviate the need for a reference biosignal recording (e.g., an electrocardiogram, ECG) for extracting hemodynamic parameters from the knee.

The aims of quantifying edema and blood-flow in the post-injury period necessitate a small form factor system obtaining accurate bioimpedance measurements from the body in an energy-efficient manner. Towards reaching that goal, a digitally-assisted analog approach was followed: designing a system benefiting from the advantages of both analog (i.e., low power) and digital (i.e., programmability) domains. The present system uses this approach to perform (i) bioimpedance measurements, (ii) calibration, and (iii) preprocessing and feature extraction.

The first function, performing the bioimpedance measurements from the body, is achieved by a custom, analog front-end designed with discrete components. A low-power TI MSP430 series microcontroller (Texas Instruments, Inc., Dallas, Tex., US) is used with a micro secure digital (SD) card as a data logger to enable processing of the signals later on a computer. The microcontroller is also used to implement the second function of the system, namely performing calibration, which aims to reduce the measurement error due to environmental changes (e.g., temperature). Feature extraction, is performed using MATLAB software (MathWorks, Natick, Mass.) to extract physiologically-relevant information from the calibrated data stored on a microSD.

Analog Front-End

Comprising resistive body fluids (e.g., blood, intra-cellular fluid) and capacitive cell-walls, the EBI of a local joint body region can be modeled, to the first order, as a single RC network. It should be noted that the RC network has a static component related to the total fluid-volume and a dynamic component related to the time-dependent fluid-volume changes (e.g., blood flow periodic with the heart beat). The analog front-end was designed to perform a single-frequency bioimpedance analysis to extract both static and dynamic components of the RC network (block diagram of front-end shown in FIG. 9).

Figure 9:
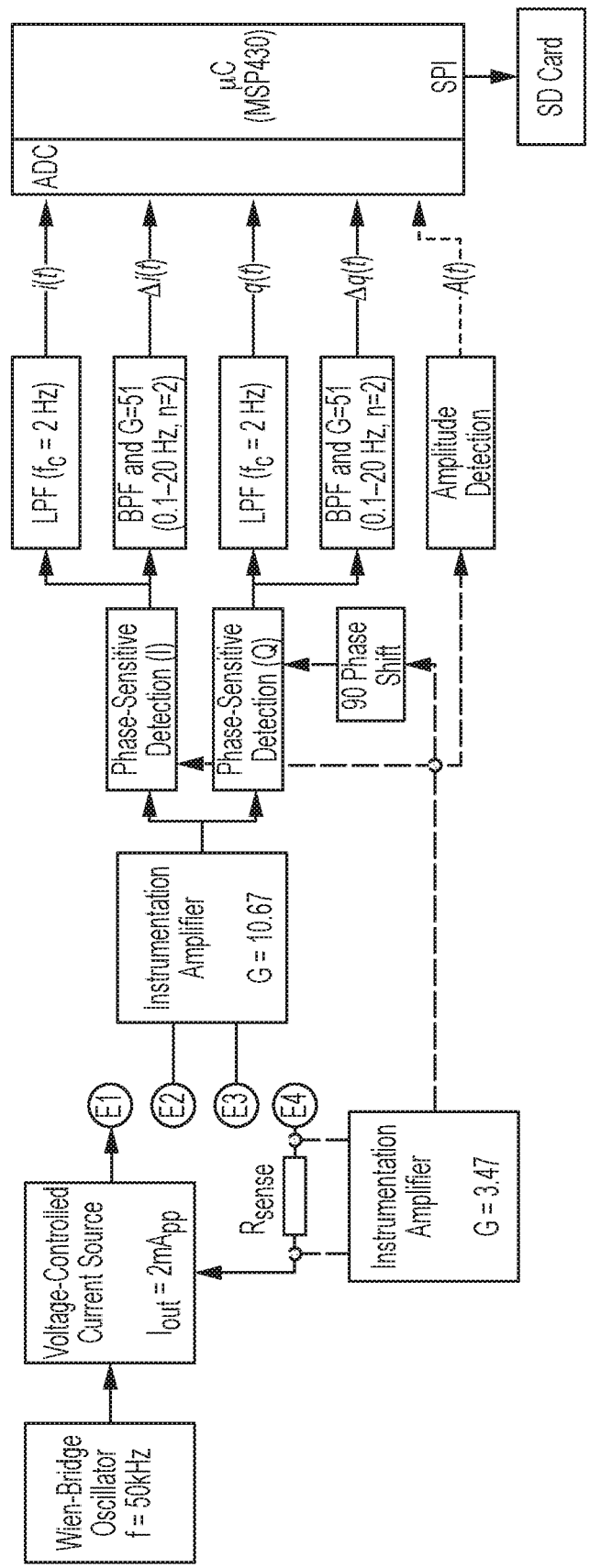
FIG. 9 is another block diagram of the bioimpedance measurement system for local joint health assessment according to an exemplary embodiment of the present invention.

In FIG. 9, E1-E4 represent the four electrodes on the body used for impedance measurement; i(t) and q(t) represent the static (slowly varying on the order of hours to days), and $\Delta i(t)$ and $\Delta q(t)$ represent the dynamic (rapidly varying on the order of milli-seconds) bioimpedance components; A(t) is the sensed electrical current delivery to the body being monitored in real-time to ensure safety and enable real-time calibration of the measured data on-board the microcontroller (μC).

The circuit excites the body with a sine wave current at $f_0$=50 kHz, a frequency that enables current to flow through both extracellular and intracellular fluid paths and therefore is widely used in single-frequency bioimpedance analysis systems. The design incorporates a diode-stabilized Wien-Bridge oscillator generating an 800 mV$_{pp}$ sinusoidal signal at 50 kHz. The voltage output of the oscillator is converted to current by a high output-impedance, high-bandwidth, voltage-controlled current source (VCCS). The VCCS delivers the current to the series combination of the body-load, $Z_{Body}$, and a small and pure resistive load of $R_{sense}$=100Ω.

To cancel out the effects of non-ideal skin-electrode interfaces on the measurements, current is injected to the joint through a quadripolar electrode configuration formed by E1-E4 in FIG. 9, where E1 and E4 are current injection and E2 and E3 are voltage measurement electrodes. Voltage measurements across $Z_{Body}$ and $R_{sense}$ are made by means of two separate instrumentation amplifier (IA) stages, IA$_{body}$ and IA$_{sense}$.

The signal at the output of the IA$_{body}$, namely $v_{Body}(t)$ is used to extract voltage measurements corresponding to both resistive and reactive components of the $Z_{Body}$ through phase-sensitive detection circuitry. A differential high-pass filter (HPF) with a cut off frequency of 7.2 kHz reduces any electromyogram (EMG) bleed-through from the surrounding muscles. The signal at the output of the IA$_{sense}$, namely $V_{sense}(t)$, is used for (i) generating the clocks that drive the phase-sensitive detection circuitry using comparators, and (ii) monitoring the magnitude of the current delivered to the body, namely $I_{pp}$, through an envelope detector formed by a diode and RC network, the output of which is the current monitoring signal A(t) in FIG. 9. The clocks for the in-phase and quadrature-phase sensitive detection are generated from the $V_{sense}(t)$ and a 90° phase shifted version of the $v_{sense}(t)$ obtained using an all-pass-filter, respectively. Both clocks are used to alternate analog switches between $v_{Body}(t)$ and $-v_{Body}(t)$.

The signal from each phase-sensitive detector is filtered to give the final output signals. For the very slowly-varying static in-phase and quadrature signals, namely i(t) and q(t), the outputs of phase-sensitive detectors are each filtered with a low-pass filter (LPF) having a cutoff frequency of $f_{-3\ dB}$=2 Hz. To extract the small-magnitude and more rapidly-varying dynamic in-phase and quadrate signals, namely $\Delta i(t)$ and $\Delta q(t)$, the signals from the phase sensitive detector are filtered by band-pass filters (BPF) with bandwidths of 0.1 Hz-20 Hz and gains of 51 V/V.

It should be noted that the sinusoidal voltage signal from the oscillator is amplified through the VCCS and the IA$_{body}$ stages, which set the mid-band gain, namely $A_{MB}$. When determining $A_{MB}$, both noise and dynamic range considerations have been taken into account. For improved noise performance, $A_{MB}$ needs to be sufficiently high. On the other hand, to obtain a large dynamic range that satisfies the linear operation of the circuit, $A_{MB}$ cannot be arbitrarily large.

For a typical knee impedance value of $R_{body}$=80Ω, high signal-to-noise ratio (SNR) signals can be obtained by setting $I_{pp}$≈2 mA, which is well below the safety threshold. However, it should be noted that $Z_{Body}$ will vary among different subjects. Therefore, the VCCS is designed as a variable-gain stage that can be tuned to ensure linear operation while not compromising the noise performance. For instance, to obtain high SNR signals from small impedance loads, $I_{pp}$ can be increased. On the other hand, for measurements from larger impedance loads, to keep the circuit in the linear region, $I_{pp}$ can be reduced. The maximum and minimum possible values of $I_{pp}$ are 3.3 mA$_{pp}$ and 0.6 mA$_{pp}$, respectively. The gain of the IA$_{body}$, namely $A_{IA,body}$, is determined based on the dynamic range constraints. Setting $A_{IA,body}$=10.67 V/V, a dynamic range of ~300Ω, which exceeds the typical maximum bioimpedance values from the knee, is achieved. The gain of the IA$_{sense}$, is set to $A_{IA,sense}$=3.47 V/V, which is sufficiently high for generating clocks at the comparator outputs.

The measurements from the analog front-end are converted to resistance and reactance values by following an automatic calibration procedure. During a measurement period, to compensate for the effects of environmental changes on the measurements, calibration is automatically repeated.

Calibration

As with any bioimpedance measurement system, a calibration procedure is necessary to map the static and dynamic voltage signals-namely i(t), q(t), $\Delta i(t)$, $\Delta q(t)$—into static and dynamic impedance signals; namely static resistance r(t), static reactance x(t), dynamic resistance $\Delta r(t)$ and dynamic reactance $\Delta x(t)$. In an ideal synchronous demodulation scheme, i(t) and q(t) would be proportional to r(t) and x(t) respectively, where the impedance being measured is r(t)+jx(t). Therefore, ideally a one-time calibration of the circuitry would be sufficient to map the measured signals to impedance values. However, changes in environmental parameters (e.g., temperature, humidity), and circuit non-idealities, adversely affect the measurement consistency along the course of a measurement. To correct measurement errors caused by changes in the excitation current, $I_{PP}$, and therefore increase the robustness of the wearable system, the impedance measurements can be scaled by a correction factor of $c_f$=2 mA/$l_{PP}$ (amplitude correction), where $I_{PP}$ is monitored by A(t). Furthermore, temperature variations also create phase delays at the clocks of the phase-sensitive detection circuitry switches, which affects both magnitude and phase of an impedance measurement. To further rule out those variations, calibration can be performed in an intermittent manner (real-time calibration) by a low-power TI MSP430 series microcontroller.

As an effort to reduce the calculation burden that real-time calibration could potentially place on the microcontroller, a computationally-efficient two-step calibration procedure is followed: (i) phase correction and (ii) ordinary least squares linear regression.

The first calibration step is correcting the phase error. The non-ideal switching time, namely $t_{sw}$>0, of the demodulator switches in phase-sensitive detection circuitry results in rotation of the measurement vector $[i(t)\ q(t)]^T$ by $\phi$ radians, where $\phi=2\pi t_{sw}f_0$. Therefore the phase error is corrected by rotating the vector by $\phi$ radians clockwise to obtain the corrected measurement vector:

$$\begin{bmatrix} \tilde{i}(t) \\ \tilde{q}(t) \end{bmatrix} = \begin{bmatrix} \cos\phi & \sin\phi \\ -\sin\phi & \cos\phi \end{bmatrix} \begin{bmatrix} i(t) \\ q(t) \end{bmatrix}, \quad (3)$$

where $\tilde{i}(t)$ and $\tilde{q}(t)$ are proportional to r (t) and x(t), respectively.

The second step aims to man the corrected measurement vector to the impedance vector:

$$\begin{bmatrix} r(t) \\ x(t) \end{bmatrix} = \begin{bmatrix} m_R \\ m_X \end{bmatrix} \begin{bmatrix} \cos\phi & \sin\phi \\ -\sin\phi & \cos\phi \end{bmatrix} \begin{bmatrix} i(t) \\ q(t) \end{bmatrix} + \begin{bmatrix} C_R \\ C_X \end{bmatrix}, \quad (4)$$

where $m_R$ and $c_R$ are the coefficients of linear regression between I(t) and r(t). Similarly $m_X$ and $c_X$ are regression coefficients for the quadrature channel.

Finding the calibration coefficients in Equation 4-namely $m_R$, $C_R$, $m_X$, $c_X$, and $\phi$-requires a series of static in-phase and quadrature measurements on test loads of known values. Four series RC test loads, which span the impedance dynamic range, with impedances $R_1=23.8\Omega$, $C_1=47$ nF; $R_2=98.2\Omega$; $R_3=56.4\Omega$, $C_3=94$ nF; $R_4=75.4\Omega$, $C_4=68$ nF are selected. The loads are connected to the analog front-end successively by means of a multiplexer controlled by the microcontroller. The phase correction step is performed by calculating $\phi=\arctan q_2/i_2$ using measurements from the purely resistive $R_2$. Then, linear regression is performed using the measurements from all four test loads to calculate the remaining calibration coefficients. The same coefficients are used to perform the mapping for the dynamic measurements:

$$\begin{bmatrix} \Delta r(t) \\ \Delta x(t) \end{bmatrix} = \frac{1}{G}\begin{bmatrix} m_R \\ m_X \end{bmatrix} \begin{bmatrix} \cos\phi & \sin\phi \\ -\sin\phi & \cos\phi \end{bmatrix} \begin{bmatrix} \Delta i(t) \\ \Delta q(t) \end{bmatrix}, \quad (5)$$

where the factor 1/G is introduced to divide out the dynamic channel output gain. The offset vector $[c_R\ c_X]^T$ in Equation 4 is filtered out by the dynamic channel output stages.

The mapped signals are then used to extract musculoskeletal and cardiovascular features from the knee joints.

Preprocessing and Feature Extraction Algorithms

The preprocessing and feature extraction is separately done for static and dynamic signals. The musculoskeletal features of tissue resistance and reactance are extracted from the static signals and the cardiovascular features of heart rate, local pulsatile blood volume and flow rate are extracted from the dynamic signals.

The preprocessing of the static signals i[n] and q[n] involves conversion to impedance signals r[n] and x[n] using Equation 4. Then, the static signals and the current monitoring signal A[n] are averaged in a 60 second window, to get $r_{avg}$, $x_{avg}$, and $A_{avg}$, respectively. The final joint resistance and reactance measurements of $R_{measured}$ and $X_{measured}$ are obtained by performing the amplitude correction explained in the calibration section on $r_{avg}$ and $x_{avg}$ using $A_{avg}$.

Figure 10:
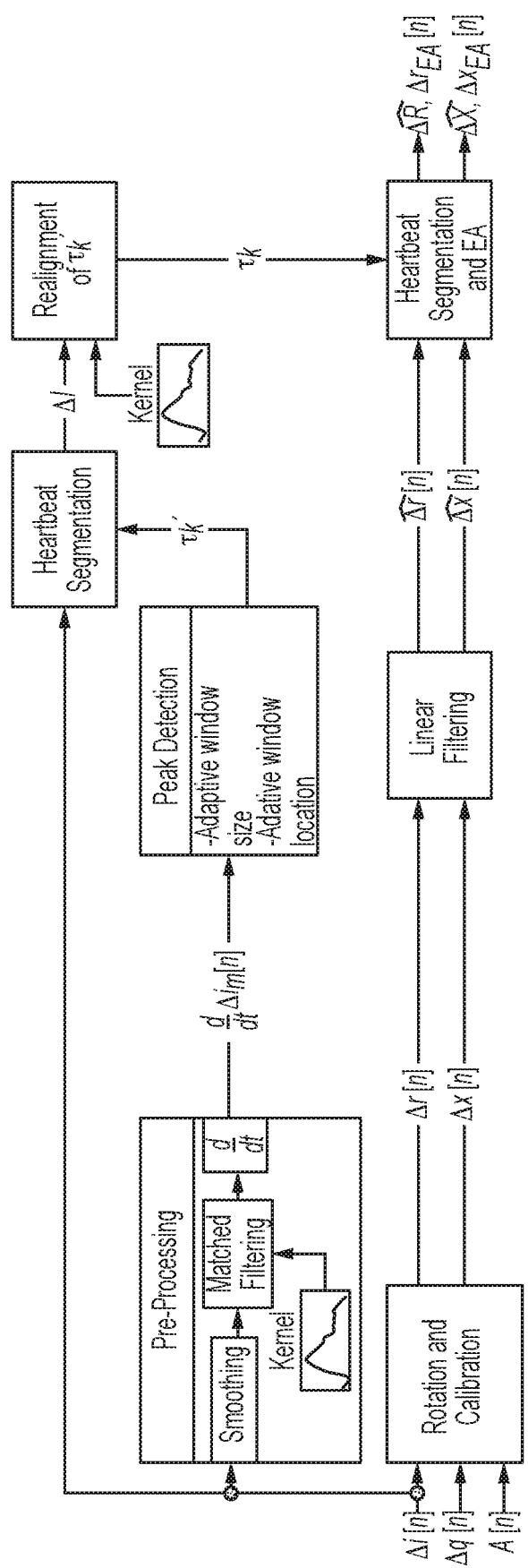
FIG. 10 is a physiology-driven algorithm design for extracting cardiovascular parameters automatically from the dynamic component (i.e. IPG) of the bioimpedance signals according to an exemplary embodiment of the present invention.

The signal processing performed on the dynamic signals involves calibration/filtering and ensemble averaging as shown in FIG. 10. FIG. 10 is a physiology-driven algorithm design for extracting cardiovascular parameters automatically from the dynamic component (i.e. IPG) of the bioimpedance signals. First, the signals are pre-processed to reduce noise and detect heartbeats; then heartbeat segmentation is used to enable ensemble averaging to further improve the signal quality; finally, features of blood volume pulse and blood flow are then extracted from these ensemble averaged vector IPG traces.

The dynamic signals, $\Delta i[n]$ and $\Delta q[n]$, are first converted to impedance signals via calibration using Equation 5. The dynamic impedance signals are then amplitude corrected using $A_{avg}$ which is followed by band-pass filtering by an FIR (finite impulse response) filter with bandwidth 0.1 Hz to 20 Hz to obtain $\widetilde{\Delta r}[n]$ and $\widetilde{\Delta x}[n]$. This step completes the calibration/filtering of the impedance signals before they are ensemble averaged.

Heartbeats from the knee are detected using $\Delta i[n]$. This signal is first smoothed using a Savitzky-Golay filter of $4^{th}$ order and 21 taps, then filtered using a matched filtering approach. The matched filter impulse response (kernel) is a clean, smoothed dynamic in-phase bioimpedance signal, also acquired from the knee previously. This kernel is stored for use and is not adaptive. The matched filtered signal is then differentiated using a Savitzky-Golay Filter of the same kind as used for the smoothing, to form the signal $$\frac{d}{dt}i_m[n].$$

The signal $$\frac{d}{dt}i_m[n]$$

is ted to a peak detection algorithm to detect heart beats. Peaks in the waveform are searched window-by-window. When a peak is found within the given window, the window size is updated using previous heartbeat intervals. The window is then moved to its next location. To make sure the heartbeats are detected precisely, the window is re-located such that the peak is around the mid-point of the given window. The peak times found are stored in a vector $\tau_k'$. The number of peaks detected per minute gives the heart rate (HR) in bpm.

The signal $\Delta i[n]$ is segmented using the peak times $\tau_k'$. The segments of $\Delta i[n]$ ($\Delta i_k[n]$) are stored in each row of the matrix $\Delta I$. The cross correlation of each segment $\Delta i_k[n]$, with the kernel is calculated. The maximum of this cross correlation is used to correct the peak times $\tau_k'$ such that each $\Delta i_k[n]$ is aligned with the kernel. The corrected peak times are stored in the vector $\tau_k$.

The peak times $\tau_k$ are used to segment $\widetilde{\Delta r}[n]$ and $\widetilde{\Delta x}[n]$. The segments $\widetilde{\Delta r_k}[n]$ and $\widetilde{\Delta x_k}[n]$ are stored in rows of the matrices $\widetilde{\Delta R}$ and $\widetilde{\Delta X}$ respectively. The ensemble average of $\widetilde{\Delta r}[n]$ is calculated by averaging the segments $\widetilde{\Delta r_k}[n]$ on a sample by sample basis equation:

$$\Delta r_{EA}[n] = \Sigma_{k=1}^N \widetilde{\Delta r_k}[n]. \quad (6)$$

The ensemble average of $\widetilde{\Delta x}[n]$ ($\Delta x_{EA}[n]$) is then calculated in an analogous manner. The ensemble averaged signals $\Delta r_{EA}[n]$ and $\Delta x_{EA}[n]$ are used for feature extraction. The peak-to-peak amplitudes of these waveforms, $\Delta r_{pp}$ and $\Delta x_{pp}$, are extracted as they might show differences in injured and healthy knees.

The signal $\Delta r_{EA}[n]$ is differentiated using the same Savitzky-Golay filter mentioned before, to obtain $$\frac{d}{dt}\Delta r_{EA}[n].$$

On me waveorms, the B, C and X points are identified. The amplitude difference between the points B and C $\left(\frac{d}{dt}\Delta r_{MAX} \text{ in } \Omega/s\right)$, the timing difference between B and X (ejection time, $T_{ET}$ in s) are used to calculate the local pulsatile blood volume $\Delta V_{blood}$ (in ml) using:

$$\Delta V_{blood} = \rho\left(\frac{L}{R_{measured}}\right)^2 T_{ER} \frac{d}{dt}\Delta r_{MAX}, \quad (7)$$

where ρ is the resistivity of blood which is taken as 135 Ωcm, L (cm) is the distance between the voltage electrodes and $R_{measured}$ (Ω), is the measured resistance of the joint. The local blood flow rate $\overline{Q}_{local}$ (in ml/min) is calculated using the equation a $\overline{Q}_{local} = \Delta V_{blood}$ HR. The cardiovascular features HR, $\Delta V_{blood}$ and $\overline{Q}_{local}$ will be used in injury assessment as discussed previously Results And Discussion Circuit Verification The designed analog front-end was fabricated on a 64 mm×48 mm PCB (FIG. 11(a)). On-board potentiometers were used such that the circuit can also be tuned for other excitation frequencies (7.5 kHz-100 kHz) and current amplitudes (0.6 $mA_{pp}$-3.3 $mA_{pp}$) as well.

To verify the calibration procedure, the measurements $i_k$ and $q_k$ were acquired from the four calibration loads mentioned previously using a 3024A oscilloscope (Keysight, Santa Rosa, Calif., US). The calibration parameters were calculated using MATLAB. Static measurements i(t) and q(t) were acquired from the same loads, 10 times within a day.

Figure 11:
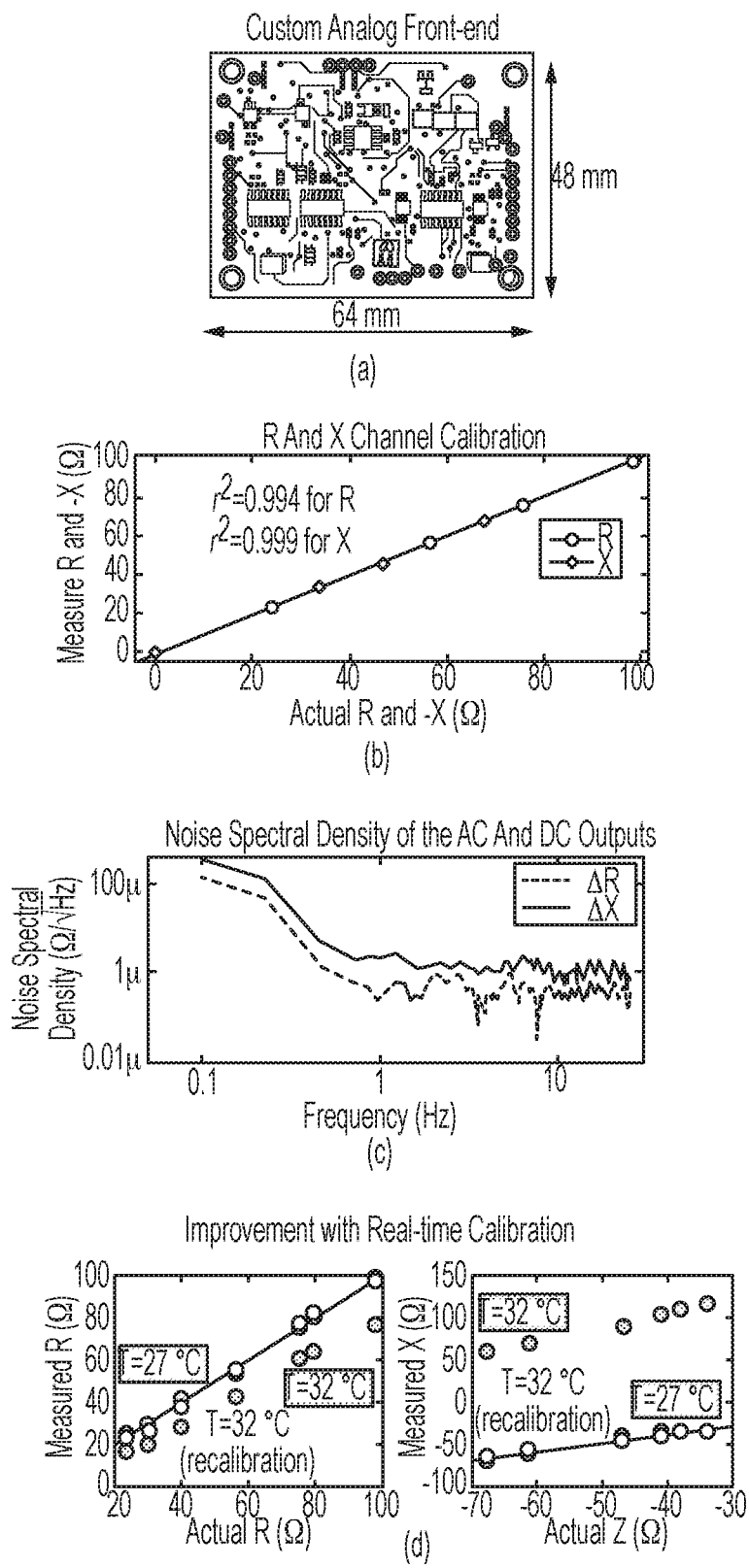
FIGS. 11(a)-(d) illustrate circuit verification. (a) Photo of the printed circuit board (PCB) fabricated for the analog front-end. (b) Calibration of the resistance and reactance measurements demonstrated high linearity and consistency (points are shown for multiple measurements taken on different days). (c) Noise spectral density plots for dynamic impedance measurements (i.e. IPG). The total noise integrated from 0.8-20 Hz was found to be 18 $\mu\Omega_{rms}$ for the resistive and 55 $\mu\Omega_{rms}$ for the reactive dynamic components, lower than any other previously reported design in the existing literature. (d) Demonstration of improvement of calibration using the innovative microcontroller-enabled automatic calibration methods according to an exemplary embodiment of the present invention.

From Equation 4, the acquired voltage measurements were converted to impedance measurements using the calculated calibration parameters. The measured versus actual resistance (R) and reactance (X) of the loads are shown in FIG. 11(b). The actual load impedances were measured using an Agilent 34410A 6½ digit multimeter. A line was fitted for the R and the X measurements separately (red lines in FIG. 11(b)). The impedance measurements made by the custom analog front-end were linear and consistent within the range 0Ω<R<100Ω and 0Ω<-X<70Ω ($R^2$≈1 for both R and X).

To measure the relative error, four impedances, different then the calibration impedances but within the same impedance range, were used. The measured impedances were compared to those measured using the multimeter. The mean relative measurement errors were 3.9% for R, 5.9% for X, 1.4% for |Z| and 1.8% for ∠Z.

Connecting a potentiometer to the circuit as a load, the dynamic range of the front-end was tested. The resistance at which the IA measuring across the potentiometer saturates, was defined as the dynamic range and was measured as 345Ω. The measured dynamic range covers the expected knee impedance values varying between 40Ω and 80Ω for R and −20Ω and −10Ω for X.

To calculate the noise floor of the measured dynamic impedances, the noise spectral densities of Δi(t) and Δq(t) were acquired using an SR785 signal analyzer (Stanford Research Systems, Sunnyvale, Calif., US) with a 0Ω load across the analog front-end. The cross spectra of Δi(t) and Δq(t) were also acquired. The voltage noise spectral densities were mapped to the noise spectral densities of Δr(t) and Δx(t) using Equations 4 and 5. The resulting noise spectral densities are shown in FIG. 11(c). The noise floor was calculated for a bandwidth of 0.1-20 Hz. The resulting noise floors were 0.018 $m\Omega_{rms}$ for Δr(t) and 0.055 $m\Omega_{rms}$ for Δx(t).

The current consumption of the front-end was measured as 132 mA when supplied by ±5 V regulated from two 9 V batteries, leading to 0.66 W power consumption. The microcontroller power consumption was measured as 150 mW when writing data to the SD card, and 33 mW when sampling with the clock frequency set to 25 MHz. Thus, the overall power consumption for the system was 0.81 W.

To evaluate the system performance, the electronic and system specifications were compared against numerous bioimpedance measurement systems (see TABLE II). The architectures used for these systems can be categorized as (i) computer assisted designs, (ii) application specific integrated circuits (ASICs), (iii) field programmable gate array (FPGA) designs, and (iv) discrete designs. Computer-assisted systems such as [1-3] cannot be classified as wearable. ASIC systems such as [4-9] are advantageous due to their small size and low power consumption, but are expensive to manufacture and limited in terms of programmability. FPGA based systems such as [10, 11] require high current levels, limiting their feasibility for wearable, continuous monitoring applications. Discrete designs such as [12-16] can provide an inexpensive, programmable alternative to existing approaches, can be rapidly prototyped and evaluated in human subjects testing, and-with the design described in this paper-can achieve sufficiently small size and low power consumption for wearable joint health monitoring systems.

TABLE II

| Reference(s) | Power Cons. (W)[a] | Noise (RTI, $m\Omega_{rms}$) | Measurement Error | Dynamic Range (Ω) | Size | Architecture[b] | Functions |
| --- | --- | --- | --- | --- | --- | --- | --- |
| [1, 2] | — | — | \|Z\|: 0.05Ω ∠Z: 0.003° | 100Ω < R < 1.1 kΩ | Non-wearable, PXI based | (i) PXI based synth. and demod. | Static/Dynamic \|Z\| and ∠Z, spectro. |
| [3] | — | — | R: 0.02Ω | 100Ω < R < 1 kΩ | Large, rack mounted modules | (i) Analog front end + computer | Static \|Z\| and ∠Z, spectro. |
| [4] | 0.0016 (FE) | — | — | 1Ω < \|Z\| < 3.5 kΩ 0° < ∠Z < 90° | 8 $cm^2$ including antenna, wearable | (ii) ASIC | Static \|Z\| and ∠Z, spectro. |
| [5] | 0.0024 (FS) | 100 | — | — | 5 $mm^2$ | (ii) ASIC | Dynamic \|Z\| |
| [6] | 0.0144 (FS) | — | R: 0.2Ω X: 0.2Ω | R < 54Ω 0.7 Ω < X < 15Ω | 4.8 × 3 $cm^2$ | (ii) ASIC | Static R and X, spectro. |

TABLE II-continued

| Reference(s) | Power Cons. (W)[a] | Noise (RTI, m$\Omega_{rms}$) | Measurement Error | Dynamic Range ($\Omega$) | Size | Architecture[b] | Functions |
|---|---|---|---|---|---|---|---|
| [7] | 0.0021 (FE) | — | — | 100$\Omega$ < \|Z\| < 10 k$\Omega$ 0° < $\angle Z$ < 30° | 6.95 mm² | (ii) ASIC | Static R and X, multi-freq. |
| [8] | 0.0034 (FS) | — | R, X: 5% | 32$\Omega$ < \|Z\| < 5.3 k$\Omega$ | 1.52 mm² | (ii) ASIC | Static R and X, multi-freq. |
| [9] | 58$\mu$ (FE) 345$\mu$ (FS) | 438 | — | — | 7 × 7 mm² | (ii) ASIC | Static R |
| [10] | 3.7 (FS) | 5 | — | R < 3.2 k$\Omega$ | 136 × 145 mm² | (iii) FPGA based | Static/Dynamic \|Z\| and $\angle Z$, spectro. |
| [11] | — | — | \|Z\|: 1.2% $\angle Z$: 0.18° | \|Z\| > 2 k$\Omega$ | — | (iii) FPGA based | Static \|Z\| and $\angle Z$ |
| [12] | — | — | \|Z\|: 1.1% $\angle Z$: 1% | R > 10 k$\Omega$ | — | (iv) AD5933 controlled by $\mu$C | Static \|Z\| and $\angle Z$, spectro. |
| [13] | — | — | R: 1% | 50$\Omega$ < R < 1.6 k$\Omega$ | Wearable | (iv) AD5933 based | Static R and X, spectro. |
| [14] | — | — | — | \|Z\| < 1 k$\Omega$ | Portable | (iv) Discrete with sync. demod. | Static \|Z\|, Dynamic \|Z\| |
| [15] | — | — | \|Z\|: 0.36$\Omega$ $\angle Z$: 0.0049° | 9$\Omega$ < \|Z\| < 5.7 k$\Omega$ 0° < $\angle Z$ < 180° | Handheld, 0.5 kg | (iv) AD8302 controlled by $\mu$C | Static \|Z\| and $\angle Z$, spectro. |
| [16] | 0.546 (FS) | — | R: 0.4$\Omega$ X: 0.3$\Omega$ | — | 145 × 40 × 4 mm³, 30 g | (iv) AD5933 based | Static R and X, spectro. |
| Present Invention | 0.66 (FE) 0.81 (FS) | 0.018 | R: 3.9% X: 5.9% \|Z\|: 1.4%, $\angle Z$: 1.8% | \|Z\| < 345$\Omega$ | 64 × 48 mm² (FE) | (iv) Discrete with, sync. demod. | Static and Dynamic R, Static and Dynamic X |

[a]FS = Full system, FE = Front-end only; Noise RTI in [5] was calculated for a bandwidth of 20 Hz using the noise spectral density reported.
[b]Architecture sorted into four groups: (i) Computer-assisted architecture; (ii) ASIC; (iii) FPGA; (iv) Discrete design.

TABLE II is a comparison of electrical and system specifications for EBI circuits and systems sorted by architecture. The references include:

[1] B. Sanchez, J. Schoukens, R. Bragos, and G. Vandersteen, "Novel Estimation of the Electrical Bioimpedance Using the Local Polynomial Method. Application to In Vivo Real-Time Myocardium Tissue Impedance Characterization During the Cardiac Cycle," *Biomedical Engineering, IEEE Transactions on*, vol. 58, pp. 3376-3385, 2011.

[2] B. Sanchez, E. Louarroudi, E. Jorge, J. Cinca, R. Bragos, and R. Pintelon, "A new measuring and identification approach for time-varying bioimpedance using multisine electrical impedance spectroscopy," *Physiological Measurement*, vol. 34, p. 339, 2013.

[3] A. Hartov, R. A. Mazzarese, F. R. Reiss, T. E. Kerner, K. S. Osterman, D. B. Williams, and K. D. Paulsen, "A multichannel continuously selectable multifrequency electrical impedance spectroscopy measurement system," *Biomedical Engineering, IEEE Transactions on*, vol. 47, pp. 49-58, 2000.

[4] J. Ramos, J. L. Ausin, A. M. Lorido, F. Redondo, and J. F. Duque-Carrillo, "A wireless, compact, and scalable bioimpedance measurement system for energy-efficient multichannel body sensor solutions," *Journal of Physics: Conference Series*, vol. 434, p. 012016, 2013.

[5] L. Yan, J. Bae, S. Lee, T. Roh, K. Song, and H.-J. Yoo, "A 3.9 mW 25-Electrode Reconfigured Sensor for Wearable Cardiac Monitoring System," *Solid-State Circuits, IEEE Journal of* vol. 46, pp. 353-364, 2011.

[6] S. Lee, S. Polito, C. Agell, S. Mitra, R. F. Yazicioglu, J. Riistama, J. Habetha, and J. Penders, "A Low-power and Compact-sized Wearable Bio-impedance Monitor with Wireless Connectivity," *Journal of Physics: Conference Series*, vol. 434, p. 012013, 2013.

[7] A. Yufera, A. Rueda, J. M. Munoz, R. Doldan, G. Leger, and E. O. Rodriguez-Villegas, "A tissue impedance measurement chip for myocardial ischemia detection," *Circuits and Systems I: Regular Papers, IEEE Transactionsion*, vol. 52, pp. 2620-2628, 2005.

[8] P. Kassanos, L. Constantinou, I. F. Triantis, and A. Demosthenous, "An Integrated Analog Readout for Multi-Frequency Bioimpedance Measurements," *Sensors Journal, IEEE*, vol. 14, pp. 2792-2800, 2014.

[9] N. Van Helleputte, M. Konijnenburg, J. Pettine, J. Dong-Woo, K. Hyejung, A. Morgado, R. Van Wegberg, T. Torfs, R. Mohan, A. Breeschoten, H. de Groot, C. Van Hoof, and R. F. Yazicioglu, "A 345uW Multi-Sensor Biomedical SoC With Bio-Impedance, 3-Channel ECG, Motion Artifact Reduction, and Integrated DSP," *Solid-State Circuits, IEEE Journal of* vol. 50, pp. 230-244, 2015.

[10] S. Kaufmann, A. Malhotra, G. Ardelt, and M. Ryschka, "A high accuracy broadband measurement system for time resolved complex bioimpedance measurements," *Physiological Measurement*, vol. 35, p. 1163, 2014.

[11] S. Sun, L. Xu, Z. Cao, H. Zhou, and W. Yang, "A high-speed electrical impedance measurement circuit based on information-filtering demodulation," *Measurement Science and Technology*, vol. 25, p. 075010, 2014.

[12] C. Margo, J. Katrib, M. Nadi, and A. Rouane, "A four-electrode low frequency impedance spectroscopy measurement system using the AD5933 measurement chip," *Physiological Measurement*, vol. 34, p. 391, 2013.

[13] F. Seoane, J. Ferreira, J. J. Sanchez, and R. Bragós, "An analog front-end enables electrical impedance spectroscopy system on-chip for biomedical applications," *Physiological Measurement*, vol. 29, p. S 267, 2008.

[14] L.-Y. Shyu, C.-Y. Chiang, C.-P. Liu, and W.-C. Hu, "Portable impedance cardiography system for real-time noninvasive cardiac output measurement," *Journal of Medical and Biological Engineering*, vol. 20, pp. 193-202, 2000.

[15] Y. Yang, J. Wang, G. Yu, F. Niu, and P. He, "Design and preliminary evaluation of a portable device for the measurement of bioimpedance spectroscopy," *Physiological Measurement*, vol. 27, p. 1293, 2006.

[16] T. Schlebusch, Ro, x, thlingsho, x, L. fer, K. Saim, Ko, x, M. ny, and S. Leonhardt, "On the Road to a Textile Integrated Bioimpedance Early Warning System for Lung Edema," in *Body Sensor Networks (BSN), 2010 International Conference on*, 2010, pp. 302-307.

As seen from TABLE II, the present invention has higher resolution in impedance measurements than all the similar conventional systems shown. This enables the present invention to sense blood-flow-related impedance changes from the knee. This high measurement resolution is achieved in an energy-efficient manner with a small footprint. Furthermore, compared with other systems in TABLE II, the present invention is the only one (that can be deployed in a wearable device) enabling real-time calibration to minimize measurement errors due to environmental changes.

Physiological Measurement Results and Discussion

Figure 12:
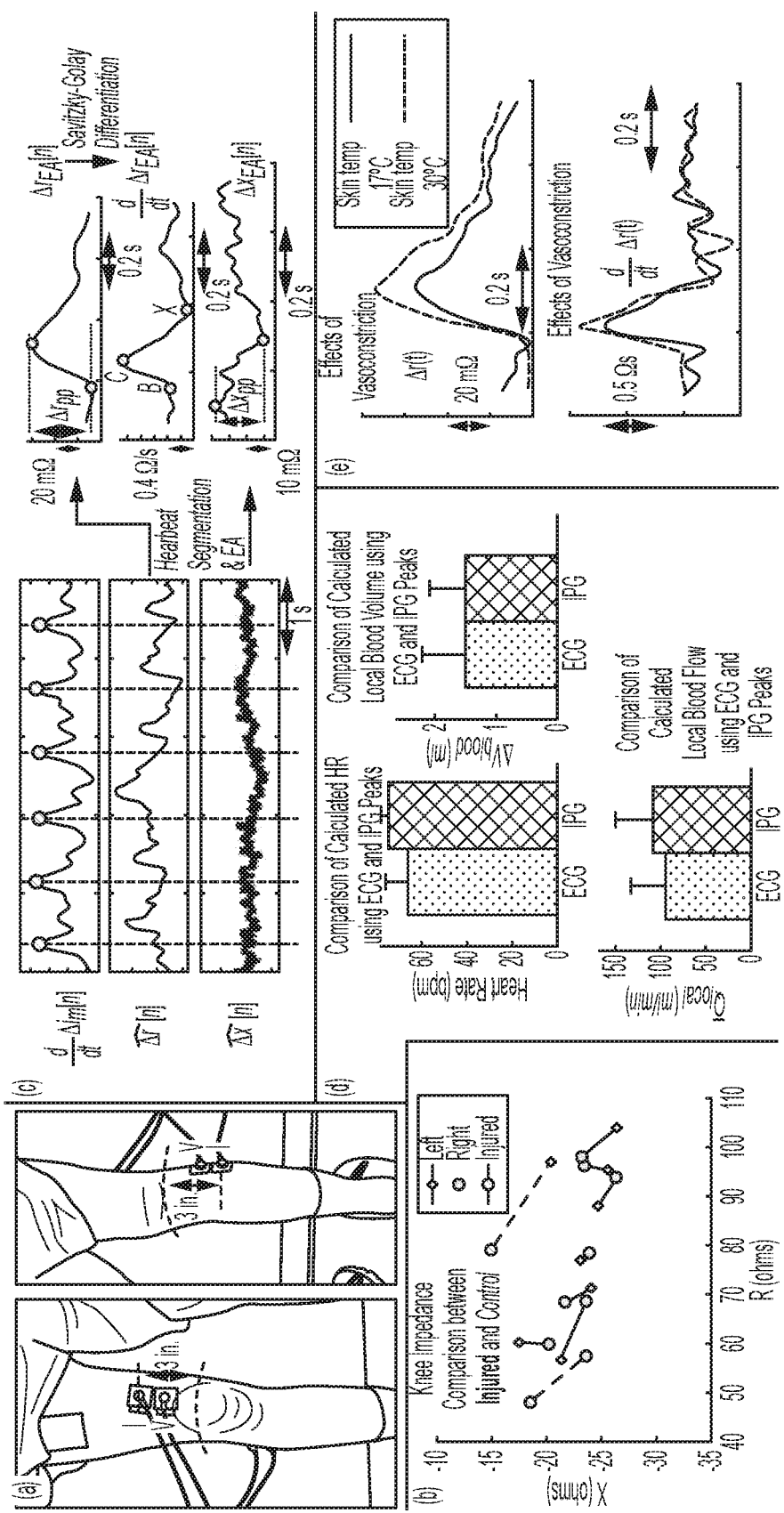
FIGS. 12(a)-(e) illustrate human subject measurements according to an exemplary embodiment of the present invention. (a) Electrode placement for knee IPG acquisition. (b) Static impedance measurements. (c) Example waveforms from the intermediate stages of the preprocessing and the feature extraction. (d) Comparison of extracted features using ECG-based vs. IPG-based ensemble averages. (e) Evaluation of the system in response to changes in physiology (vasoconstriction after 2 minutes cold pressor test).

Human subject testing was performed on nine subjects; seven control subjects with no recent history of injuries to the knees and two injured subjects with recent unilateral knee injuries (ACL or meniscal tear). The studies were approved by the Georgia Institute of Technology IRB as well as the AHRPO. The circuit was interfaced to the body via Ag/AgCl gel electrodes, positioned as shown in FIG. 12(*a*). The proximal current electrode was placed three inches above the crease on the quadriceps tendon, towards the inner side of the knee. The distal current electrode was placed three inches below the crease on the popliteal fossa, towards the outer side of the knee. The voltage electrodes were placed adjacent to the current electrodes. To evaluate the ensemble averaging algorithm, ECG signals from the control group were acquired using a BioNomadix (Biopac Systems Inc, Goleta, Calif., US) wireless ECG acquisition module.

All signals acquired were recorded on Biopac data acquisition hardware and processed on MATLAB. For the human subject studies, a one-time calibration followed by amplitude correction was performed.

During the testing protocol, each subject sat upright with his/her back resting against the wall and legs extended forward. While the subject was still, 90 seconds of the signals i(t), q(t), $\Delta$i(t), $\Delta$q(t), A(t) and the ECG (for the control group) were acquired from both knees separately. The data between 20 s and 80 s were processed to rule out any motion artifacts at the beginning and the end of the measurement cycle (from initial positioning of the body). For pulsatile blood volume calculations, the distance between the voltage electrodes on each knee were measured.

Figure 13:
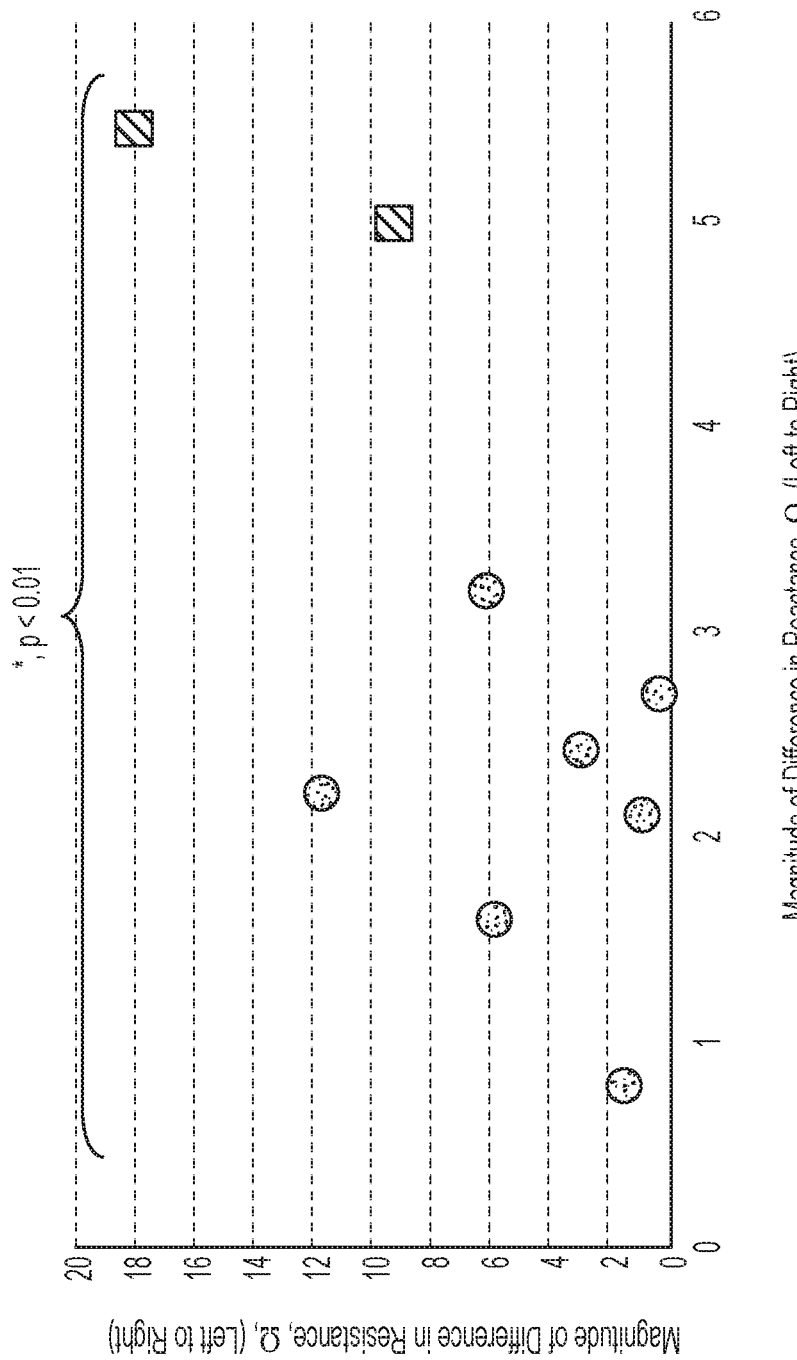
FIG. 13 is a graph of the magnitude of difference in resistance versus reactance between the left and right leg for control subjects (circle markers) versus following acute knee injury (square markers) according to an exemplary embodiment of the present invention. This small feasibility study already demonstrated a statistically significant difference between the populations, as evident by the clear separation between the groups, and in accordance with prior studies in the existing literature with bench-top bioimpedance measurement circuits.

The resulting static impedances for each knee from each subject are plotted in FIG. 12(*b*), and the differences between the magnitude of resistance and reactance in left versus right knee are shown in FIG. 13. The left versus the right knee impedances of nearly all control subjects were within 12$\Omega$ from each other in the R and 3.2$\Omega$ from each other in the X axes. The difference between the resistance and reactance of the left and the right knees had no statistical significance for the control group. However, even for the small feasibility study sample size of two injured subjects, there was a significant difference (p<0.01) in the impedances of the involved and contralateral knee compared to the control group. The injured side on both subjects had lower resistance, R, by an average of 13.7$\Omega$ and negative reactance, -X, by an average of 5.25$\Omega$. These results are consistent with physiological expectations (reduced resistance due to increased edema, reduced negative reactance associated with damaged cell membranes).

The pre-processing and feature extraction algorithms described were used to calculate the cardiovascular features HR, $\Delta V_{blood}$ and $\overline{Q}_{local}$ for the control group. The signals obtained at intermediate and final steps of the ensemble averaging algorithm are presented in FIG. 12(*c*). The accurate detection of heart beats enabled the dynamic (IPG) impedance signals to be segmented accurately. Therefore, high SNR waveforms were obtained after ensemble averaging leading to clear detection of B, C, and X points.

These features were also calculated using an ECG-assisted ensemble averaging algorithm for comparison. It was observed that the cardiovascular features calculated with and without the ECG were consistent (FIG. 12(*d*)) with no statistically significant differences observed. Furthermore, no significant differences were observed in the cardiovascular features on the injured side compared to the contralateral side.

For one of the control subjects, a separate experiment was performed to examine the effects of vasoconstriction on the dynamic impedance signal measured from one knee. Specifically, the methodology was analogous to a cold pressor test, with the subject's bare foot being submerged in ice water while the IPG signal was measured across the knee (not submerged) to increase downstream peripheral vascular resistance (PVR). The purpose of this experiment was to evaluate the sensitivity with which the system developed in this work could detect minute changes in knee joint blood flow associated with modified downstream PVR.

The subject's skin temperature was measured on the bare foot prior to submerging and found to be 30° C. The impedance signals were acquired from the knee for 60 seconds while the subject was seated, with the tested leg extended and resting on a support. The foot of the same side was immersed into ice water until the foot skin temperature dropped to 17° C. The foot was taken out of the cold water and impedance signals were again recorded for 60 seconds from the knee in the same position as before.

A plot of the resistance signal ensemble averaged using the algorithm described above ($\Delta r_{EA}(t)$) and its derivative $$\left(\frac{d}{dt}\Delta r_{EA}(t)\right)$$

taken using a Savitzky-Golay filter are shown in FIG. 12(*e*). The minute changes in this IPG signal associated with downstream vasoconstriction can be observed on both waveforms as a significant drop in amplitude (20 m$\Omega$ decrease for the resistance, and 0.2 $\Omega$/s decrease for the time derivative of resistance). Accordingly, the system was sufficiently sensitive to detect both the reduction in local blood volume pulse and blood flow with increased PVR, consistent with physiological expectations.

CONCLUSIONS

The present invention incorporates a discrete design for high resolution EBI measurements from the knee joint based on embedded systems concepts. The combined use of high performance analog front-end electronics and digital programmability using a microcontroller allow high quality static (slowly varying over the course of hours to days) and dynamic (rapidly varying on the order of milli-seconds) impedance measurements on a platform that is appropriate for a wearable device.

The overall system was designed and demonstrated from end-to-end, including the design of the circuit, customized physiology-driven algorithms for detecting features from the measured signals, and human subjects experiments to both evaluate the capabilities in detecting small changes in local bioimpedance due to edema and modified blood flow. The invention includes the mechanical packaging to encapsulate the electronics in a wearable sleeve around the knee joint, and collect data serially during the recovery from acute knee joint injury. The present wearable system based on the engineering foundation herein presented enables high resolution, quantitative assessment of both the structural and hemodynamic characteristics of the knee joint longitudinally for the first time, paving the way to better understanding joint recovery physiology, and designing closed-loop personalized therapies to accelerate the recovery process.

Numerous characteristics and advantages have been set forth in the foregoing description, together with details of structure and function. While the invention has been disclosed in several forms, it will be apparent to those skilled in the art that many modifications, additions, and deletions, especially in matters of shape, size, and arrangement of parts, can be made therein without departing from the spirit and scope of the invention and its equivalents as set forth in the following claims. Therefore, other modifications or embodiments as may be suggested by the teachings herein are particularly reserved as they fall within the breadth and scope of the claims here appended.

What is claimed is:

1. A system for assessing joint health of a joint comprising:
    a first sensing assembly for sensing characteristics related to the joint health comprising a wearable sensor for placement proximate the joint and configured to measure at least one non-acoustic characteristic of the joint during movement;
    a second sensing assembly for sensing characteristics related to the joint structure comprising:
        a first wearable bioimpedance sensor comprising a source of current; and
        a second wearable bioimpedance sensor comprising a receiver and configured for placement proximate the joints;
    the second sensing assembly configured to measure bioimpedance of the joint based at least in part upon a voltage drop across the joint;
    a health assessor that provides an assessment of joint health through interpretation of characteristics from the first and the second sensing assemblies; and
    an output assembly capable of providing an indication of joint health to a user of the system;
    wherein:
        at least one non-acoustic characteristic of the joint during movement is selected from the group consisting of linear acceleration and angular velocity;
        the first sensing assembly further comprises an acoustic sensor configured to measure acoustic emissions from the joint during movement; and
        the health assessor is configured to automatically and periodically calibrate the measured bioimpedance from the second sensing assembly.

2. The system of claim 1 further comprising an output assembly capable of providing an indication of joint health to a user of the system.

3. The system of claim 1, wherein the first sensing assembly further comprises a wearable acoustic sensor configured to measure acoustic emissions from the joint during movement.

4. The system of claim 1, wherein a non-acoustic characteristic of the joint during movement is selected from the group consisting of linear acceleration and angular velocity.

5. The system of claim 1, wherein the second sensing assembly further comprises a processor configured to measure a potential difference across the joint through amplification and phase-sensitive detection stages, the potential difference reflective of the bioimpedance of tissue and blood in proximity of the joint.

6. The system of claim 1, wherein the acoustic sensor comprises a wearable acoustic sensor for placement proximate the joint.

7. The system of claim 6, wherein the wearable acoustic sensor comprises piezoelectric film and is capable of measuring surface vibrations of skin associated with acoustic emissions from the joint.

8. The system of claim 1, wherein the acoustic sensor comprises a sensor for placement distal the joint.

9. The system of claim 8, wherein the acoustic sensor distal the joint comprises a microphone capable of measuring airborne acoustic emissions from the joint.

10. The system of claim 1, wherein the health assessor comprises a health assessor processor selected from the group consisting of a processor that:
    automatically and periodically calibrates bioimpedance measurements using electronic loads and an algorithm;
    processes at least one signal representative of acoustic emissions from the joint in the context of joint angle;
    processes acoustic emissions from the joint using filter banks to separate signals based on frequency content;
    detects a type of activity occurring in proximity to the joint, and processes acoustic emissions from the joint during the activity based on the type of activity;
    processes at least one signal representative of bioimpedance of the joint, which processing provides an indication of joint swelling;
    processes at least one signal representative of bioimpedance of the joint, which processing provides an indication of blood flow proximate the joint; and
    processes at least one signal representative of bioimpedance of the joint, which processing provides an indication of blood volume proximate the joint.

11. The system of claim 10, wherein the health assessor processor detects a type of activity occurring in proximity to the joint, and processes acoustic emissions from the joint during the activity based on the type of activity; and
    wherein a type of activity is selected from the group consisting of unloaded knee flexion/extension exercise, sit-to-stand exercise, walking, and stair-climbing.

12. The system of claim 1, wherein:
the system is a wearable system for assessing joint health of a user;
the health assessor quantifies a degree of injury at the joint through interpretation of characteristics from the first and the second sensing assemblies; and
the second sensing assembly and health assessor are capable of determining one or more of joint swelling, blood flow proximate the joint, and blood volume proximate the joint.

13. The system of claim 12 further comprising an output assembly capable of providing an indication of joint health to the user of the system.

14. The system of claim 12 further comprising an output assembly capable of providing an indication of joint health to a care giver of the user of the system.

15. The system of claim 1, wherein:
the system is for assessing joint health of a user;
the first sensing assembly comprises a first sensing modality assembly, the first sensing modality assembly comprising an acoustical assembly including:
wearable proximate joint acoustic sensors capable of sending at least one signal representative of acoustic emissions from the joint during movement;
distal joint acoustic sensors capable of sending at least one signal representative of airborne acoustic emissions from the joint during movement; and
the wearable sensor for placement proximate the joint and configured to measure at least one non-acoustic characteristic of the joint during movement, wherein the wearable sensor is capable of sending at least one signal representative of at least one non-acoustic characteristic of joint movement selected from the group consisting of linear acceleration and angular velocity;
the second sensing assembly comprises a second sensing modality assembly, the second sensing modality assembly comprising a bioimpedance assembly that includes the first and second wearable bioimpedance sensors configured to measure bioimpedance of the joint; and
the bioimpedance assembly and health assessor are capable of determining characteristics related to joint structure selected from the group consisting of joint swelling, blood flow, and blood volume.

16. The system of claim 15, wherein the bioimpedance assembly further comprises a processor capable of measuring the potential difference across the joint through amplification and phase-sensitive detection stages.

17. The system of Claim 16, wherein the first wearable bioimpedance sensor comprises two electrodes configured for current injection;
wherein the second wearable bioimpedance sensor comprises two electrodes configured for voltage measurement; and
wherein the electrodes of the first and second wearable bioimpedance sensors comprise a quadripolar configuration to reduce the effect of electrode-skin interface impedance.

18. The system of claim 15, wherein the first wearable bioimpedance sensor comprises at least two electrodes.

19. The system of Claim 18, wherein the first wearable bioimpedance sensor delivers current below a safety threshold that does not create damage at the joint.

20. The system of Claim 18, wherein the first wearable bioimpedance sensor delivers current at a frequency such that it can propagate through both intra and extra-cellular fluids.

21. The system of claim 15, wherein the blood flow characteristic comprises a static component and a dynamic component.

22. The system of claim 21, wherein the static component of the blood flow characteristic relates to relatively slow-varying fluid volume.

23. The system of claim 21, wherein the dynamic component of the blood flow characteristic relates to relatively fast-varying blood flow rate.

24. The system of claim 15, wherein the wearable proximate joint acoustic sensors comprise contact microphones that capture sound waves originated by mechanical vibrations in proximity of the joint.

25. A system for assessing joint health of a joint comprising:
a first sensing assembly for sensing characteristics related to the joint physiology, the first sensing assembly comprising:
acoustic sensors configured to measure acoustic emissions from the joint during movement, wherein at least one of the acoustic sensors comprises a wearable acoustic sensor for placement proximate the joint and capable of measuring surface vibrations of skin associated with acoustic emissions from the joint, and wherein at least one of the acoustic sensors comprises a microphone distal the joint and capable of measuring airborne acoustic emissions from the joint; and
sensors configured to measure at least one non-acoustic characteristic of joint movement selected from the group consisting of linear acceleration and angular velocity;
a second sensing assembly for sensing characteristics related to the joint structure by measuring bioimpedance of the joint, the second sensing assembly comprising:
a first bioimpedance sensor comprising two electrodes configured for current injection:
a second bioimpedance sensor comprising two electrodes configured for voltage measurement; and
a processor configured to measure a potential difference across the joint through amplification and phase-sensitive detection stages;
wherein the four electrodes of the first and second bioimpedance sensors are in a quadripolar electrode configuration;
a health assessor configured to:
detect a type of activity occurring in proximity to the joint;
process acoustic emissions from the joint during the activity based on the type of activity; and
provide an assessment of joint health through interpretation of characteristics from the first and the second sensing assemblies including the detection of the type of activity and the processing of the acoustic emissions; and
an output assembly capable of providing an indication of the joint health to a user of the system;
wherein at least one sensor that is configured to measure at least one non-acoustic characteristic of the joint during movement, and the electrodes of the second bioimpedance sensor, each comprise wearable sensors for placement proximate the joint.

26. The system of claim 25, wherein at least a portion of the wearable sensors comprise surface silver/silver-chloride (Ag/AgCl) gel electrodes.

27. The system of claim 25, wherein at least a portion of the wearable sensors comprise capacitive dry electrodes.

28. The system of claim 25, wherein at least a portion of the wearable sensors comprise textile electrodes.

* * * * *